United States Patent
Taghibiglou et al.

(10) Patent No.: US 11,300,566 B2
(45) Date of Patent: Apr. 12, 2022

(54) ADAM-10 AS A BIOMARKER FOR DETECTING BRAIN INJURY

(71) Applicant: University of Saskatchewan, Saskatoon (CA)

(72) Inventors: Changiz Taghibiglou, Saskatoon (CA); Nathan Pham, Saskatoon (CA); Landon Pastushok, Martensville (CA); Clarence Ronald Geyer, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 0 days.

(21) Appl. No.: 15/737,846

(22) PCT Filed: Jun. 30, 2016

(86) PCT No.: PCT/CA2016/050771
§ 371 (c)(1),
(2) Date: Dec. 19, 2017

(87) PCT Pub. No.: WO2017/000073
PCT Pub. Date: Jan. 5, 2017

(65) Prior Publication Data
US 2018/0321243 A1 Nov. 8, 2018

Related U.S. Application Data

(60) Provisional application No. 62/186,511, filed on Jun. 30, 2015.

(51) Int. Cl.
*G01N 33/573* (2006.01)
*C07K 16/40* (2006.01)
*G01N 33/68* (2006.01)
*C07K 16/28* (2006.01)

(52) U.S. Cl.
CPC ....... *G01N 33/573* (2013.01); *C07K 16/2896* (2013.01); *C07K 16/40* (2013.01); *C12Y 304/24081* (2013.01); *G01N 33/6896* (2013.01); *G01N 2333/96486* (2013.01); *G01N 2800/28* (2013.01)

(58) Field of Classification Search
CPC ............ G01N 33/573; G01N 33/6896; G01N 2800/28; C07K 16/40
See application file for complete search history.

(56) References Cited

PUBLICATIONS

Zetterberg, H., & Blennow, K. (2016). Fluid biomarkers for mild traumatic brain injury and related conditions. Nature Reviews Neurology, 12(10), 563-574.

Agoston, DV & Elsayed, M. "Serum-based protein biomarkers in blast-induced traumatic brain injury spectrum disorder." Front Neurol., Jul. 6, 2012, vol. 3:107 [online], ISSN 1664-2295, [retrieved on Jul. 20, 2016 (Jul. 20, 2016)]. Retrieved from the Internet: <URL: http://journal.frontiersin.org/article/10.3389/fneur.2012.00107/full>.

ADAM10: Human A Disintegrin And Metalloprotease 10 ELISA Kit—Biotin Detection Antibody Format 96T. Product sheet [online]. FIVEphoton Biochemicals, 2013 [retrieved on Jul. 20, 2016 (Jul. 20, 2016)]. Retrieved from the Internet: <URL :http://fivephoton.com/pdfs/Fivephoton%20Human%20ADAM10%20ELISA%20Kit%20Protocol%20-%20Biotin%20Detection.pdf>.

Pham, Nam et al., "Plasma ADAM10 level as a potential biomarker for traumatic brain injury", Abstract, presented at the 10th Canadian Association for Neuroscience meeting in Toronto, May 29-Jun. 1, 2016.

Pham, Nam et al., "Plasma ADAM10 level as a potential biomarker for traumatic brain injury", Poster, presented at the 10th Canadian Association for Neuroscience meeting in Toronto, May 29-Jun. 1, 2016.

Altmeppen HC, Prox J, Puig B, Kluth MA, Bernreuther C, Thurm D, Jorissen E, Petrowitz B, Bartsch U, De Strooper B, Saftig P and Glatzel M. Lack of a-disintegrin-and-metalloproteinase ADAM10 leads to intracellular accumulation and loss of shedding of the cellular prion protein in vivo. Molecular Neurodegeneration 2011; 6:36.

Bauman RA, Ling G, Tong L, et al. An introductory characterization of a combat-casualty-care relevant swine model of closed head injury resulting from exposure to explosive blast. J Neurotrauma 2009; 26: 841-60.

Belanger HG, Vanderploeg RD, Curtiss G, Warden DL. Recent neuroimaging techniques in mild traumatic brain injury. J Neuropsychiatry Clin Neurosci. 2007, 19: 5-20.

Boden BP, Tacchetti RL, Cantu RC, Knowles SB, Mueller FO. Catastrophic head injuries in high school and college football players. Am J Sports Med. 2007, 35: 1075-1081.

Brookings Institution, Saban Center for Middle East Policy. Iraq index: tracking variables of reconstruction and security in post-Saddam Iraq. Apr. 27, 2010.

Burtis CA et al. Tietz Textbook of Clinical Chemistry and Molecular Diagnostics, 5th Edition, 2012, p. 106, Elsevier publication.

(Continued)

*Primary Examiner* — Olga N Chernyshev
(74) *Attorney, Agent, or Firm* — Melanie Swerzas; Ainslie Parsons; Bereskin & Parr LLP/S.E.N.C.R.L., s.r.l.

(57) ABSTRACT

The present disclosure relates to a method for detecting a brain injury in a subject by comparing the amount of ADAM10 protein in a blood sample from the subject to a reference standard or to the amount of ADAM10 in a blood sample from a control. An increase in the amount of ADAM10 in the subject blood sample relative to the reference standard or control is indicative of the subject having sustained a brain injury, in particular a traumatic brain injury (TBI). The present disclosure also provides novel antibody and antibody fragments that bind to ADAM10 at different positions.

12 Claims, 9 Drawing Sheets
Specification includes a Sequence Listing.

(56) References Cited

PUBLICATIONS

Caffey J. The whiplash shaken infant syndrome: manual shaking by the extremities with whiplash-induced intracranial and intraocular bleedings, linked with residual permanent brain damage and mental retardation. Pediatrics. Oct. 1974;54(4):396-403.

Chavko M, Koller WA, Prusaczyk WK, et al. Measurement of blast wave by a miniature fiber optic pressure transducer in the rat brain. J Neurosci Methods 2007; 159:277-81.

Cole SP. Monoclonal antibodies. Can Fam Physician. Feb. 1987;33:369-72.

Daneshvar DH, Nowinski CJ, McKee AC, Cantu RC. The epidemiology of sport-related concussion. Clin Sports Med. 2011, 30: 1-17, vii.

Elder GA, Mitsis EM, Ahlers ST, Cristian A. Blast-induced mild traumatic brain injury. Psychiatr Clin N Am. 2010; 33: 757-81.

Endres K and Fahrenholz F. Regulation of alpha-secretase ADAM10 expression and activity. Exp Brain Res. 2012; 217: 343-352.

Forde CT, Karri SK, Young AM, Ogilvy CS. Predictive markers in traumatic brain injury: opportunities for a serum biosignature. Br J Neurosurg. 2014; 28: 8-15.

Gavett BE, Stern RA, McKee AC. Chronic traumatic encephalopathy: a potential late effect of sport-related concussive and subconcussive head trauma. Clin Sports Med. 2011, 30: 179-188, xi.

Guingab-Cagmat JD, Cagmat EB, Hayes RL, Anagli J. Integration of proteomics, bioinformatics, and systems biology in traumatic brain injury biomarker discovery. Front Neurol. 2013; 4: 61.

Guskiewicz KM, Register-Mihalik J, McCrory P, McCrea M, Johnston K, et al. Evidence-based approach to revising the SCAT2: introducing the SCAT3. Br J Sports Med. 2013; 47: 289-293.

Halstead ME, Walter KD. American Academy of Pediatrics. Clinical report—sport-related concussion in children and adolescents. Pediatrics. 2010; 126: 597-615.

Harmon KG, Drezner J, Gammons M, Guskiewicz K, Halstead M, et al. American Medical Society for Sports Medicine position statement: concussion in sport. Clin J Sport Med. 2013; 23: 1-18.

Hoge CW, McGurk D, Thomas JL, et al. Mild traumatic brain injury in U.S. soldiers returning from Iraq. N Engl J Med. 2008; 358:453-6.

Huse WD, Sastry L, Iverson SA, et al. Generation of a large combinatorial library of the immunoglobulin repertoire in phage lambda. Science. 1989; 246: 1275-81.

Jeter CB, Hergenroeder GW, Hylin MJ, Redell JB, Moore AN, et al. Biomarkers for the diagnosis and prognosis of mild traumatic brain injury/concussion. J Neurotrauma. 2013; 30: 657-670.

Kohler G, Milstein C. Continuous cultures of fused cells secreting antibody of predefined specificity. Nature. 1975; 256, 495-497.

Kozber D, Roder JC. The production of monoclonal antibodies from human lymphocytes. Immunology Today.1983; 4 (3):72-79.

Langlois JA, Rutland-Brown W, Wald MM. The epidemiology and impact of traumatic brain injury: a brief overview. J Head Trauma Rehabil. 2006; 21: 375-378.

Mathivanan S, Ji H, and Simpson RJ. Exosomes: Extracellular organelles important in intercellular communication. Journal of Proteomics. 2010; 73(10): 1907-1920.

McKee AC, Daneshvar DH, Alvarez VE, Stein TD. The neuropathology of sport. Acta Neuropathol. 2014; 127: 29-51.

Meehan WP, 3rd, Mannix RC, O'Brien MJ, Collins MW. The prevalence of undiagnosed concussions in athletes. Clin J Sport Med. 2013; 23: 339-342.

Okie, S. Traumatic brain injury in the war zone. N. Engl. J. Med. 2005; 352, 2043-2047.

Pham N, Sawyer TW, Wang Y, Jazii FR, Vair C, Taghibiglou C. Primary blast-induced traumatic brain injury in rats leads to increased prion protein in plasma: a potential biomarker for blast-induced traumatic brain injury. J Neurotrauma. 2015; 32:58-65.

Pham N, Akonasu H, Shishkin R, Taghibiglou C. Plasma soluble prion protein, a potential biomarker for sport-related concussions: a pilot study. PLoS One. 2015;10:e0117286.

Schardin H. The physical principles of the effects of a detonation. German aviation medicine, World War II. Washington DC: Department of the US Air Force. Office of the Surgeon General; 1950: 1207-24.

Strathmann FG, Schulte S, Goerl K, Petron DJ Blood-based biomarkers for traumatic brain injury: Evaluation of research approaches, available methods and potential utility from the clinician and clinical laboratory perspectives. Clin Biochem. 2014; 47(10-11):876-88.

Tanielian T, Jaycox LH. Invisible wonds of war: Psychological and cognitive injuries, their consequences and services to assist recovery. Rand Corp, MG 720-CCF, 2008; Santa Monica, CA.

Van Der Pol E, Böing AN, Harrison P, Sturk A, and Nieuwland R. Classification, Functions, and Clinical Relevance of Extracellular Vesicles. Pharmacol Rev. 2012; 64:676-705.

Vingtdeux V and Marambaud P. Identification and biology of α-secretase. Journal of Neurochemistry. 2012; 120 (Suppl. 1): 34-45.

Ward RL, Clark MA, Lees J, Hawkins NJ. Retrieval of human antibodies from phage-display libraries using enzymatic cleavage. J Immunol Methods. 1996; 189: 73-82.

Warden D. Military TBI during the Iraq and Afghanistan wars. J Head Trauma Rehabil. 2006; 21: 398-402.

Warren KM, Reeves TM, and Phillips LL. MT5-MMP, ADAM-10, and N-Cadherin Act in Concert To Facilitate Synapse Reorganization after Traumatic Brain Injury. Journal of Neurotrauma. 2012; 29(10); 1922-1940.

Wolf SJ, Bebarta VS, Bonnett CJ, Pons PT, Cantrill SV. Blast injuries. Lancet, 2009; 374; 405-15.

Wolf H, Frantal S, Pajenda GS, Salameh O, Widhalm H, et al. Predictive value of neuromarkers supported by a set of clinical criteria in patients with mild traumatic brain injury: S100B protein and neuron-specific enolase on trial: clinical article. J Neurosurg. 2013; 118: 1298-1303.

Yarnell AM, Shaughness MC, Barry ES, et al. Blast traumatic brain injury in the rat using a blast overpressure model. Current Protocols in Neurosci. 2013; 9.41: Supplement 62.

Yokobori S, Hosein K, Burks S, Sharma I, Gajavelli S, et al. Biomarkers for the clinical differential diagnosis in traumatic brain injury—a systematic review. CNS Neurosci Ther. 2013; 19: 556-565.

Zetterberg H, Smith DH, Blennow K. Biomarkers of mild traumatic brain injury in cerebrospinal fluid and blood. Nat Rev Neurol. 2013; 9: 201-210.

Zhang Si, Kojic L, Tsang M, et al. Distinct roles for metalloproteinases during traumatic brain injury. Neurochem. Intl. 2016; 96:46-55.

Zohar O, Lavy R, Zi X, Nelson TJ, Hongpaisan J, Pick CG, Alkon DL. PKC activator therapeutic for mild traumatic brain injury in mice. Neurobiology of Disease. 2011; 41(2); 329-337.

Musumeci Giuseppe et al: "Characterization of matrix metalloproteinase-2 and -9, ADAM-10 and N-cadherin expression in human glioblastoma multiforme", Cell and Tissue Research, Springer, DE, vol. 362, No. 1, May 7, 2015, pp. 45-60.

Bulstrode Harry et al: "A-Disintegrin and Metalloprotease (ADAM) 10 and 17 promote self-renewal of brain tumor sphere forming cells", Cancer Letters, vol. 326, No. 1, Dec. 29, 2012, pp. 79-87.

Agoston, D.V. and Elsayed, M. Serum-based protein biomarkers in blast-induced traumatic brain injury spectrum disorder, Frontiers in Neurology, Jul. 6, 2012, vol. 3:107 [online], [retrieved on Jul. 20, 2016]. Retrieved from the Internet: <URL: http://journal.frontiersin.org/article/10.3389/fneur.2012.00107/full> <DOI: 10.3389/fneur.2012.00107>.

ADAM10: Human A Disintegrin And Metalloprotease 10 ELISA Kit—Biotin Detection Antibody Format 96T. Product sheet [online]. FIVEphoton Biochemicals, 2013 [retrieved on Jul. 20, 2016]. Retrieved from the Internet: <URL: www.fivephoton.com/pdfs/Fivephoton%20Human%20ADAM10%20ELISA%20Kit%20Protocol%20-%20Biotin%20Detection.pdf>.

TBI: Get the Facts. Traumatic Brain Injury & Concussion. Centers for Disease Control and Prevention, Apr. 27, 2017 [online], [retrieved Oct. 11, 2018]. Retrieved from the Internet: <URL: http://www.cdc.gov/traumaticbraininjury/get_the_facts.html>.

(56) References Cited

PUBLICATIONS

Kim et al: Evaluation of current post-concussion protocols, Biomedicine & Pharmacotherapy, available online Jul. 16, 2020, published Sep. 2020, vol. 129, Article 110406.

Misch et al: "Sports Medicine Update: Concussion", Emerg Med Clin N Am, Feb. 2020, vol. 38, pp. 207-222.

Levin et al: "Diagnosis, prognosis and clinical management of mild traumatic brain injury", Lancet Neurol, published online Mar. 20, 2015, vol. 14, pp. 506-517.

William P. Meehan III, MD: "Medical Therapies for Concussion", NIH-PA Author Manuscript, Con Sports Med., Jan. 2011, vol. 30(1):115-ix, doi:10.1016/j.csm.2010.08.003.

Makdissi et al: "Approach to investigation and treatment of persistent symptoms following sport-related concussion: a systematic review", Br J Sports Med, published online on May 8, 2017, vol. 51, pp. 958-968; doi:10.1136/bjsports-2016-097470.

ADAM-10 AS A BIOMARKER FOR DETECTING BRAIN INJURY

CROSS-REFERENCE TO RELATED APPLICATIONS

This application is a national phase entry of PCT/CA2016/050771 filed Jun. 30, 2016 (which designates the U.S.), which claims the benefit, of priority to U.S. Provisional Application No. 62/186,511 filed Jun. 30, 2015, the contents of which are incorporated herein by reference in their entirety.

INCORPORATION OF SEQUENCE LISTING

A computer readable form of the Sequence Listing "13764-P51069USOO_SequenceListing.txt" (12,271 bytes), submitted via EFS-WEB and created on Dec. 11, 2017, is herein incorporated by reference.

FIELD

The disclosure relates to the field of biomarkers. More specifically the disclosure relates to biomarkers useful in detecting or diagnosing brain injury.

BACKGROUND

Traumatic brain injury (TBI) has been a prevalent issue for coalition forces serving in the wars in Afghanistan and Iraq. It is estimated that 15-28% of returning veterans have sustained a TBI through these conflicts (Okie 2005; Hoge et al., 2008). TBI is associated with long-term disabilities and psychiatric diseases and is often described as the 'signature injury' of these wars (Alvarez 2008; Tanielian and Jaycox, 2008), largely as a result of increased survival rates of service members thanks to advances in medical interventions and protective equipment (Regan 2004; Warden 2006). There are various causes for TBI, with 68% of military cases reported due to blast exposure (Hoge et al., 2008). Blast exposure can be a consequence of standard military ordinances, grenades, landmines or, as prominently seen throughout the recent wars, from attacks using improvised explosive devices (IEDs), accounting for about 40% of coalition deaths and a similar number of TBI cases in Iraq (Brookings Institution 2008). Worldwide estimates of terrorist attacks in both warzones and civilian settings increased four-fold from 1999-2006, with related injuries increasing eight-fold (Wolf et al., 2009). The common characteristic of IEDs is the immense wave of blast overpressure produced. At the point of detonation, there is an instantaneous expansion of gas, producing a blast wave outwards faster than the speed of sound, accompanied by a blast wind that can reach speeds over several hundred km/h (Elder et al., 2010; Wolf et al., 2009).

The underlying mechanisms of how blast waves affect the brain are not fully understood. Animal studies have established that the blast wave is transmitted through the skull to the brain (Bauman et al., 2009; Chavko et al., 2007). Schardin described explosive inertial (shearing) forces in which tissues of varying densities move at different speeds in response to a blast; thus, as the wave passes through an organ, structural components of different densities can be tethered and damaged by this shearing force (Schardin 1950; Wolf et al., 2009). Furthermore, closed-space explosions, such as within or surrounding buildings, result in higher injury severity and mortality when compared in open-space due to the increased magnitude and duration by reflected blast waves off multiple surfaces (Leibovici et al., 1996). Thus, there is a strong likelihood that those sustaining TBI in Afghanistan and Iraq have experienced such shearing forces in the brain.

Traumatic brain injury (TBI) is also the leading cause of death in North America for individuals between the ages of 1 to 45. U.S. estimates from the Center for Disease Control report 1.7 million cases of TBI annually, contributing to a third of all injury-related deaths (CDC 2012). Patients suffering from head trauma are managed according to standardized guidelines based on their Glasgow Coma Scale (GCS). Computerized tomography (CT) scan is the imaging method of choice in head trauma and is able to detect brain hematomas and skull fractures. Current guidelines recommend head CT scan in all patients with GCS 14 or less. Patients are treated based on their neurologic status and findings on their CT scan. Large epidural hematomas (>30 ml in volume) and subdural hematomas >10 mm in thickness or associated with more than 5 mm in midline shift should be surgically evacuated. Patients with epidural hematomas and GCS score ≤8 who have pupillary abnormalities and patients with subdural hematomas who have GCS score ≤8 or whose GCS scored has decreased by ≥2 points from the time of admission are also candidates for surgery. Evacuation of intracranial hemorrhage is recommended if it is in the posterior fossa. Open skull fractures and depressed skull fractures, with displacement more than the thickness of the cranium, are also treated surgically. A course of prophylactic anti-epileptic treatment is recommended in all patients with brain hematomas for 7 days.

Concussion is a complex pathophysiological process and is considered as a subset of mild traumatic brain injury (mTBI). It causes a transient disturbance of brain function resulting in less severe brain injury. Concussions are the consequence of a direct or indirect blow that results in a sudden angular acceleration or deceleration of the brain tissue within the calvarium. In the United States alone, 3.8 million cases of sport-related concussions occur annually and high-contact sports such as American football, hockey, rugby, soccer, and basketball have among the highest incidence of concussion (Daneshvar et al., 2011; Harmon et al., 2013; Langlois et al., 2006; Meehan et al., 2011). Considering unreported cases, it is highly likely that the incidence of sport-related concussions is even higher (Meehan et al., 2013).

Clinical manifestations of sport-related concussions may include a variety of symptoms such as loss of consciousness, headache, dizziness, amnesia, nausea, confusion, fatigue, sleep disturbances, balance and memory impairment, slurred speech, and light sensitivity. At the molecular pathophysiological levels, most of these symptoms are direct or indirect results of significant alterations in ionic balance, neurotransmitter activation, axonal integrity, and energy metabolism in the CNS (McKee et al., 2014).

Although most sport-related concussions are benign and athletes typically will fully recover if they get adequate rest, multiple concussions in a short period of time may lead to devastating long-term sequelae and prolonged functional impairment, including post-concussive syndrome, neurodegenerative diseases, chronic traumatic encephalopathy, as well as rare catastrophic consequences called second impact syndrome (Boden et al., 2007; Gavett et al., 2011; Halstead et al., 2010). Second impact syndrome is a post-concussion cerebral edema, which results in coma and severe neurological deficits and is often deadly. Thus, it is absolutely essential to manage concussions properly and to avoid repetitive concussive events in those who have already experienced mTBI. Since most mTBI cases show no abnormalities on computed tomography (CT) and conventional magnetic resonance imaging (MRI), identifying those athletes affected by concussion remains a challenging issue for coaches and sport medicine specialists (Belanger et al., 2007). A promising approach to ease these challenges has focused on the detection of protein biomarkers of sport-related concussion. Protein biomarkers are readily accessible in biological fluids such as plasma and serum, which may serve as valuable tools in identifying concussive athletes at greater risk for deterioration and in the guidance of immediate post-concussion therapeutic interventions as well as decision making on return to play. Several potential protein biomarkers have been identified for TBI, of which a few have been tested in sport related concussion (reviewed in Forde et al., 2014; Guingab-Cagmat et al., 2013; Jeter et al., 2013; Strathmann et al., 2014; Wolf at al., 2013; Yokobori et al., 2013; Zetterberg et al., 2013). Among these potential protein biomarkers, S100B, cleaved tau (C-tau), glial fibrillary acidic protein (GFAP), neuron-specific enolase (NSE), Myelin-basic protein (MBP), Ubiquitin C-terminal hydrolase-L1(UCH-L1), αII-spectrin breakdown products (SBDPs), Interleukin-6 (IL-6) and tumor necrosis factor-alpha (TNF-α) have been more widely studied (reviewed in Yokobori et al., 2013; Zetterberg et al., 2013).

SUMMARY

The present inventors describe a novel method for quantifying ADAM10 proteins in a blood sample to detect brain injury associated with increased ADAM10 protein. The present inventors have also identified three single chain variable fragments (scFv) that bind to the ADAM10 protein, and have confirmed that they bind to different regions of the ADAM10 protein.

Accordingly, the disclosure provides a method of detecting brain injury in a test subject comprising (a) contacting a blood sample from the test subject with a probe that binds to ADAM10 and (b) detecting and/or quantifying the amount of ADAM10, wherein an increase in the amount of ADAM10 compared to a control is indicative of the test subject having suffered a brain injury. In an embodiment the method further comprises obtaining a blood sample from the subject prior to contacting the blood sample with the probe in (a). In some embodiments the method further comprises treating the subject for brain injury if the amount of ADAM10 in the blood sample of the subject is increased compared to the control. In some embodiments, the blood sample from the test subject is obtained within and up to six days after a suspected traumatic brain injury event.

In one embodiment the control is a reference baseline level of ADAM10 of the same test subject, such as a level of ADAM10 determined prior to the test subject having a brain injury and a greater amount of ADAM10 relative to the control is indicative of the test subject having a brain injury. In an embodiment, the test subject is an athlete and the reference baseline level of ADAM10 of the subject is from the off-season. In another embodiment the control is a reference baseline level of ADAM10 of an athlete population in the off-season. In one embodiment, the control is a reference baseline level of ADAM10 of the general population. In another embodiment the control is a reference baseline level of a population of similar age and/or of the same sex.

In an embodiment the method comprises testing a series of serially diluted samples of known amounts of ADAM10.

In another embodiment is provided a method of monitoring a subject with a brain injury comprising:
(i) (a) contacting a blood sample from the subject obtained at a first time point with a probe that binds to ADAM10;
(b) detecting and/or quantifying the amount of ADAM10 at the first time point;
(ii) (a) contacting a blood sample from the subject obtained at a second time point with a probe that binds to ADAM10;
(b) detecting and/or quantifying the amount of ADAM10 at the second time point; and
(iii) comparing the amount of ADAM10 from the first time point with the amount of ADAM10 at the second time point; wherein an increase in the amount of ADAM10 indicates an increase in the severity of the brain injury and wherein a decrease in the amount of ADAM10 indicates an improvement in the brain injury.

In an embodiment the method further comprises obtaining a blood sample from the subject prior to contacting the blood sample with the probe in (i)(a) and/or (ii)(a). In one embodiment the method further comprises testing a series of serially diluted samples of known amounts of ADAM10 at the same time as quantifying (i)(b) and/or (ii)(b).

In yet another embodiment is provided a method of determining whether a subject has suffered a brain injury due to an injury event comprising:
(i) (a) contacting a blood sample from the subject obtained at a first time point prior to the injury event with a probe that binds to ADAM10;
(b) detecting and/or quantifying the amount of ADAM10 at the first time point;
(ii) (a) contacting a blood sample from the subject obtained at a second time point after the injury event with a probe that binds to ADAM10;
(b) detecting and/or quantifying the amount of ADAM10 at the second time point; and
(iii) comparing the amount of ADAM10 from the first time point with the amount of ADAM10 at the second time point; wherein an increase in the amount of ADAM10 indicates that the subject has suffered a brain injury due to the injury event. In some embodiments the second time point is within and up to six days after the injury event.

In an embodiment the method further comprises obtaining a blood sample from the subject prior to contacting the blood sample with the probe in (i)(a) and/or (ii)(a). In one embodiment the first time point provides a baseline level of the subject and the second time point is following the injury event. In an embodiment the method further comprises testing a series of serially diluted samples of known amounts of ADAM10 at the same time as quantifying (i)(b) and/or (ii)(b).

In some embodiments, the amount of ADAM10 is quantified, for example, by fluorescence, radioactivity or spectrophotometry depending on the label or marker used. In an embodiment, the amount of ADAM10 is quantified by a radioimmunoassay, an enzyme-linked immunoassay, a competitive binding enzyme-linked immunoassay, dot blot, or Western blot, or other assays known in the art. In another embodiment, a suitable detection technology such as a complementary metal-oxide-semiconductor (CMOS) or charge coupled device (CCD) is used and a unique wavelength of light is applied for illumination of the signal. In some embodiments, the method further comprises testing a series of known reference standards, such as serially diluted samples containing known amounts of ADAM10, optionally at the same time, wherein the amount of ADAM10 in the test subject sample or control sample is quantified by comparing to said reference standards.

In one embodiment, the probe is in solution. In another embodiment, the probe is immobilized on a solid support or support pad, such as filter paper, a multiwell plate or a microchip.

In one embodiment, the probe is an antibody or antibody fragment that binds to ADAM10. In an embodiment, the antibody or antibody fragment that binds to ADAM10 comprises the heavy chain CDR sequences of SEQ ID NOs: 6, 7 and 8 and/or functional variants thereof and the light chain CDR sequences of SEQ ID NOs: 1, 2 and 3 and/or functional variants thereof. In another embodiment, the antibody or antibody fragment that binds to ADAM10 comprises the heavy chain CDR sequences of SEQ ID NOs: 6, 7 and 9 and/or functional variants thereof and the light chain CDR sequences of SEQ ID NOs: 1, 2 and 4 and/or functional variants thereof. In yet another embodiment, the antibody or antibody fragment that binds to ADAM10 comprises the heavy chain CDR sequences of SEQ ID NOs: 6, 7 and 10 and/or functional variants thereof and the light chain CDR sequences of SEQ ID NOs: 1, 2 and 5 and/or functional variants thereof.

In another embodiment, the antibody or antibody fragment that binds to ADAM10 comprises the amino acid sequence as shown in SEQ ID NO:12 or functional variants thereof or is encoded by the nucleic acid sequence as shown in SEQ ID NO:11 or functional variants thereof. In yet another embodiment, the antibody or antibody fragment that binds to ADAM10 comprises the amino acid sequence as shown in SEQ ID NO:14 or functional variants thereof or is encoded by the nucleic acid sequence as shown in SEQ ID NO:13 or functional variants thereof. In a further embodiment, the antibody or antibody fragment that binds to ADAM10 comprises the amino acid sequence as shown in SEQ ID NO:16 or functional variants thereof or is encoded by the nucleic acid sequence as shown in SEQ ID NO:15 or functional variants thereof.

In an embodiment, the antibody fragment is a single chain variable fragment (scFv).

In some embodiments, contacting the blood sample from the subject with a probe comprises:

(1) contacting the sample with a first probe that binds to ADAM10 at a first position; and (2) contacting the ADAM10 bound to the first probe with a second probe that binds to ADAM10 at a second position; wherein the first or second probe is detectable. In an embodiment, the first probe is an antibody or fragment thereof that specifically binds to ADAM10 and the second probe is an antibody or fragment thereof that specifically binds to ADAM10 at a different epitope than the immobilized probe. In an embodiment, the first probe is immobilized on a solid support and the second probe is in solution and is detectable. In an embodiment, the first probe is an antibody or antibody fragment that binds to ADAM10 comprising the heavy chain CDR sequences of SEQ ID NOs: 6, 7 and 8 and/or functional variants thereof and the light chain CDR sequences of SEQ ID NOs: 1, 2 and 3 and/or functional variants thereof and the second probe is an antibody or antibody fragment that binds to ADAM10 comprising the heavy chain CDR sequences of SEQ ID NOs: 6, 7 and 9 and/or functional variants thereof and the light chain CDR sequences of SEQ ID NOs: 1, 2 and 4 and/or functional variants thereof, or vice versa. In another embodiment, the first probe is an antibody or antibody fragment that binds to ADAM10 comprising the amino acid sequence as shown in SEQ ID NO:12 or functional variants thereof or is encoded by the nucleic acid sequence as shown in SEQ ID NO:11 or functional variants thereof and the second probe is an antibody or antibody fragment that binds to ADAM10 comprising the amino acid sequence as shown in SEQ ID NO:14 or functional variants thereof or is encoded by the nucleic acid sequence as shown in SEQ ID NO:13 or functional variants thereof, or vice versa. In yet another embodiment, the first probe is an antibody or antibody fragment that binds to ADAM10 comprising the heavy chain CDR sequences of SEQ ID NOs: 6, 7 and 8 and/or functional variants thereof and the light chain CDR sequences of SEQ ID NOs: 1, 2, and 3 and/or functional variants thereof and the second probe is an antibody or antibody fragment that binds to ADAM10 comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the first probe is an antibody or antibody fragment that binds to ADAM10 comprising the amino acid sequence as shown in SEQ ID NO:12 or functional variants thereof or is encoded by the nucleic acid sequence as shown in SEQ ID NO:11 or functional variants thereof and the second probe is an antibody or antibody fragment that binds to ADAM10 comprising the amino acid sequence as shown in SEQ ID NO:16 or functional variants thereof or is encoded by the nucleic acid sequence as shown in SEQ ID NO:15 or functional variants thereof, or vice versa. In yet a further embodiment, the first probe is an antibody or antibody fragment that binds to ADAM10 comprising the heavy chain CDR sequences of SEQ ID NOs: 6, 7 and 9 and/or functional variants thereof and the light chain CDR sequences of SEQ ID NOs: 1, 2, and 4 and/or functional variants thereof and the second probe is an antibody or antibody fragment that binds to ADAM10 comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the first probe is an antibody or antibody fragment that binds to ADAM10 comprising the amino acid sequence as shown in SEQ ID NO:14 or functional variants thereof or is encoded by the nucleic acid sequence as shown in SEQ ID NO:13 or functional variants thereof and the second probe is an antibody or antibody fragment that binds to ADAM10 comprising the amino acid sequence as shown in SEQ ID NO:16 or functional variants thereof or is encoded by the nucleic acid sequence as shown in SEQ ID NO:15 or functional variants thereof, or vice versa.

In an embodiment, a double antibody-sandwich technique is applied and the amount of ADAM10 in the test subject sample is quantified by comparing the level to reference standards.

In one embodiment, the detectable probe comprises an enzyme and enzymatic activity can be used to detect and quantify the amount of ADAM10 in the sample and in the control. In some embodiments, the detectable probe comprises a biotin conjugated to the antibody or antibody fragment thereof. For example, in one embodiment, the antibody or antibody fragment thereof is conjugated to biotin and is complexed with the biotin-binding-protein avidin conjugated to an enzyme such as horse radish peroxidase (HRP). HRP activity can oxidize a chromogenic substrate 3,3',5,5'-Tetramethylbenzidine (TMB) to yield a blue colour which, upon adding stop solution (typically a sulfuric or phosphoric acid solution), turns to yellow, the intensity of which is indicative of the amount of activity of the enzyme and can be measured by spectrophotometry at an absorbance of 450 nm.

In some embodiments, the subject is a human. In an embodiment, the subject is a child.

In some embodiments, the brain injury is a traumatic brain injury. In an embodiment the traumatic brain injury is a result of an explosion, transportation accident, or sports-related concussion.

In some embodiments, the blood sample is plasma or serum.

The disclosure also relates to a kit for analyzing a blood sample to detect brain injury, said kit comprising:
(a) a probe that detects an amount of ADAM10 in a blood sample; and
(b) instructions for use in analyzing the blood sample to detect brain injury.

In an embodiment of the kit, the probe is an antibody or antibody fragment that binds to ADAM10 disclosed herein. In an embodiment, the probe is labeled for detection by radioactivity, fluorescence or absorbance. In an alternative embodiment, a secondary binding ligand is used, such as a second antibody or biotin/avidin ligand binding agent, as is known in the art for detection of the probe.

In some embodiments, the amount of ADAM10 is quantified, for example, by fluorescence, radioactivity or spectrophotometry depending on the label or marker used and the kit comprises reagents for such detection. In an embodiment, the amount of ADAM10 is quantified by a radioimmunoassay, an enzyme-linked immunoassay, a competitive binding enzyme-linked immunoassay, dot blot, Western blot, or biolayer interferometry (BLI) or other assays known in the art and the kit comprises reagents for such assays. In another embodiment, a suitable detection technology such as a complementary metal-oxide-semiconductor (CMOS) or charge coupled device (CCD) is provided with the kit or instructions for such use and a unique wavelength of light is applied for illumination of the signal.

In one embodiment, the probe is in solution. In another embodiment, the probe is immobilized on a solid support or support pad, such as filter paper, a multiwell plate or a microchip.

In another embodiment a kit is provided comprising:
(a) an immobilized probe that binds to ADAM10 at a first position;
(b) a detectable probe that binds to ADAM10 at a second position; and
(c) instructions for use in analyzing a blood sample to detect brain injury.

In an embodiment, the immobilized probe is an antibody or antibody fragment that specifically binds to ADAM10 and the detectable probe is an antibody or antibody fragment in solution that specifically binds to ADAM10 at a different epitope than the immobilized probe. In an embodiment, the probe that binds to ADAM10 at a first position is an antibody or antibody fragment comprising the heavy chain CDR sequences of SEQ ID NOs: 6, 7 and 8 and/or functional variants thereof and the light chain CDR sequences of SEQ ID NOs: 1, 2 and 3 and/or functional variants thereof and the probe that binds to ADAM10 at the second position is an antibody or antibody fragment comprising the heavy chain CDR sequences of SEQ ID NOs: 6, 7 and 9 and/or functional variants thereof and the light chain CDR sequences of SEQ ID NOs: 1, 2 and 4 and/or functional variants thereof; or vice-versa. In another embodiment, the probe that binds to ADAM10 at a first position comprises the amino acid sequence as shown in SEQ ID NO:12 or functional variants thereof or is encoded by the nucleic acid sequence as shown in SEQ ID NO:11 or functional variants thereof and the probe that binds to ADAM10 at the second position is an antibody or antibody fragment comprising the amino acid sequence as shown in SEQ ID NO:14 or functional variants thereof or is encoded by the nucleic acid sequence as shown in SEQ ID NO:13 or functional variants thereof, or vice versa. In yet another embodiment, the probe that binds to ADAM10 at a first position is an antibody or antibody fragment comprising the heavy chain CDR sequences of SEQ ID NOs: 6, 7 and 8 and/or functional variants thereof and the light chain CDR sequences of SEQ ID NOs: 1, 2, and 3 and/or functional variants thereof and the probe that binds to ADAM10 at a second position is an antibody or antibody fragment comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the probe that binds to ADAM10 at a first position comprises the amino acid sequence as shown in SEQ ID NO:12 or functional variants thereof or is encoded by the nucleic acid sequence as shown in SEQ ID NO:11 or functional variants thereof and the probe that binds to ADAM10 at a second position comprises the amino acid sequence as shown in SEQ ID NO:16 or functional variants thereof or is encoded by the nucleic acid sequence as shown in SEQ ID NO:15 or functional variants thereof, or vice versa. In yet a further embodiment, the probe that binds to ADAM10 at a first position is an antibody or antibody fragment comprising the heavy chain CDR sequences of SEQ ID NOs: 6, 7 and 9 and/or functional variants thereof and the light chain CDR sequences of SEQ ID NOs: 1, 2, and 4 and/or functional variants thereof and the probe that binds to ADAM10 at a second position is an antibody or antibody fragment comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the probe that binds to ADAM10 at a first position comprises the amino acid sequence as shown in SEQ ID NO:14 or functional variants thereof or is encoded by the nucleic acid sequence as shown in SEQ ID NO:13 or functional variants thereof and the probe that binds to ADAM10 at a second position comprises the amino acid sequence as shown in SEQ ID NO:16 or functional variants thereof or is encoded by the nucleic acid sequence as shown in SEQ ID NO:15 or functional variants thereof, or vice versa.

In some embodiments the kit further comprises serially diluted samples of ADAM10 to be used as standards for quantifying the amount of ADAM10 and optionally, the instructions provided include a step of testing the serially diluted samples optionally at the same time as the test sample.

In a further embodiment, there is provided a use of ADAM10 in a blood sample as a biomarker to detect a brain injury. Also provided is use of a probe that binds to ADAM10 in a blood sample for detecting a brain injury. In an embodiment the brain injury is a traumatic brain injury. In a further embodiment, the blood sample is plasma or serum.

Also provided herein are isolated antibodies and fragments thereof that bind ADAM10 protein.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DETAILED DESCRIPTION

Figure 1:
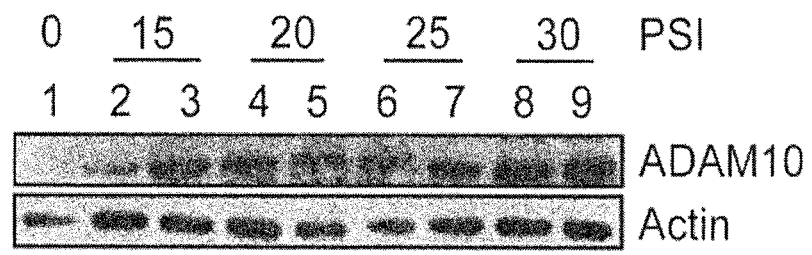
FIG. 1 shows a Western blot of ADAM10 compared to an actin control. Results are semi-quantitative and are for the purpose of simple visualization of an increased amount of ADAM10 in serum samples from rats exposed to a 15, 20, 25, or 30 PSI blast in the restraint condition relative to control serum samples from rats not exposed to blast (0 PSI).

The present inventors have shown an increased amount of ADAM10 in the blood or serum of rats subjected to a blast overpressure model, in particular in whiplash and restraint treatment groups. Whiplash condition simulates displacement of the head and/or neck due to abrupt acceleration/deceleration forces. Whiplash may be caused by any motion similar to motor vehicle rear-end collisions, amusement park rides, sports injuries, other modes of transportation, falls, or from being hit or violently shaken. Shaken baby syndrome can also result in a whiplash injury (Caffey 1972). The restraint condition simulates victims in a condition that only their heads are exposed to a blast shock wave (mostly military or conflict-zone related TBI), in which there is no significant displacement of the head. The present inventors have also shown an increased amount of ADAM10 in the blood of athletes that have suffered a brain injury, i.e. a concussion, compared to randomly selected control non-athletes (age and sex matched).

Methods/Uses/Kits

Accordingly, the disclosure provides a method of detecting brain injury in a test subject comprising (a) contacting a blood sample from the test subject with a probe that binds to ADAM10, and (b) detecting and/or quantifying the amount of ADAM10, wherein a difference or similarity in the amount of ADAM10 compared to a control is indicative of the test subject having suffered a brain injury. In some embodiments the method further comprises treating the subject for brain injury or selecting therapy for brain injury if the amount of ADAM10 in the blood sample of the subject is increased compared to the control.

As used herein, the term "blood" or "blood sample" includes whole blood and blood components, such as plasma or serum.

As used herein, the term "ADAM10" refers to Disintegrin and metalloproteinase domain-containing protein 10, also known as CDw156 or CD156c, which is a member of the ADAM family. Members of the ADAM family are cell surface proteins possessing both potential adhesion and protease domains. GenBank Accession numbers for human ADAM10 include AA126254 and AF009615 and NCBI reference IDs for nucleic acid sequences plus predicted protein sequences of human ADAM10 include NG_033876 and NM_001110. The GenBank accession number for rat ADAM10 is EDL84174 and the Swiss-Prot accession number for rat ADAM10 is Q10743.

As used herein, the term "brain injury" refers to an injury to the brain caused by a sudden force or impact, also called "traumatic brain injury", and includes without limitation injuries caused by IEDs, transportation accidents, head banging, excessive shaking, falls and sports-related head injuries, such as concussions. "mTBI" as used herein refers to a minor traumatic brain injury where there is no visible skull wound and generally has no conclusive difference by imaging. Both blast induced and sports related injuries may be minor traumatic brain injuries.

The phrase "detecting a brain injury" also refers to detecting a brain injury in a pre-symptomatic subject. "Detecting a brain injury" also includes detecting the severity of the brain injury.

In one embodiment, the methods described herein include obtaining a blood sample from a subject. Methods of obtaining blood samples are well known in the art.

The methods described herein include the identification of ADAM10 in the blood of a subject. The presence of ADAM10 can be detected using a number of methods. In one embodiment, ADAM10 proteins are detected using probes that specifically bind to and/or interact with ADAM10.

As used herein, the term "probe that binds to ADAM10" includes both direct and indirect binding to ADAM10.

As used herein, the term "probe" refers to any agent that binds, directly or indirectly, to an ADAM10 protein and is detectable either directly or indirectly.

In one embodiment, the probe is an antibody or antibody fragment that binds to ADAM10. Antibodies that bind to ADAM10 are well known in the art. Examples of antibodies that bind to ADAM10 include but are not limited to a polyclonal anti-ADAM10 antibody raised against residues 700 to the C-terminus of human ADAM10 (antibody ab84595, commercially available from Abcam Inc., Toronto, ON, Canada) and a monoclonal antibody against rat ADAM10 (commercially available in an ELISA kit from MyBioSource Inc., San Diego, Calif., USA).

In another embodiment, the antibody or antibody fragment that binds to ADAM10 comprises the heavy chain CDR sequences of SEQ ID NOs: 6, 7 and 8 and/or functional variants thereof and the light chain CDR sequences of SEQ ID NOs: 1, 2 and 3 and/or functional variants thereof. In another embodiment, the antibody or antibody fragment that binds to ADAM10 comprises the heavy chain CDR sequences of SEQ ID NOs: 6, 7 and 9 and/or functional variants thereof and the light chain CDR sequences of SEQ ID NOs: 1, 2 and 4 and/or functional variants thereof. In yet another embodiment, the antibody or antibody fragment that binds to ADAM10 comprises the heavy chain CDR sequences of SEQ ID NOs: 6, 7 and 10 and/or functional variants thereof and the light chain CDR sequences of SEQ ID NOs: 1, 2 and 5 and/or functional variants thereof.

In another embodiment, the antibody or antibody fragment that binds to ADAM10 comprises the amino acid sequence as shown in SEQ ID NO:12 or a functional variant thereof or is encoded by the nucleic acid sequence as shown in SEQ ID NO:11 or a functional variant thereof. In yet another embodiment, the antibody or antibody fragment that binds to ADAM10 comprises the amino acid sequence as shown in SEQ ID NO:14 or a functional variant thereof or is encoded by the nucleic acid sequence as shown in SEQ ID NO:13 or a functional variant thereof. In a further embodiment, the antibody or antibody fragment that binds to ADAM10 comprises the amino acid sequence as shown in SEQ ID NO:16 or a functional variant thereof or is encoded by the nucleic acid sequence as shown in SEQ ID NO:15 or a functional variant thereof.

In one embodiment, the antibody fragment is a Fab, Fab', F(ab')2, Fv or scFv. In a particular embodiment, the antibody fragment is a single chain variable fragment (scFv).

The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques and the fragments screened for utility in the same manner as described below. For example, F(ab')2 fragments can be generated by treating antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

In certain embodiments, the antibody or antibody fragment comprises all or a portion of a heavy chain constant region, such as an IgG1, IgG2, IgG3, IgG4, IgA1, IgA2, IgE, IgM or IgD constant region. In one embodiment, the heavy chain constant region is an IgG1 heavy chain constant region. Furthermore, the antibody or antibody fragment can comprise all or a portion of a kappa light chain constant region or a lambda light chain constant region. In one embodiment, the light chain constant region is a kappa light chain constant region. In one embodiment, the heavy and light chain constant regions are different from the heavy and light chain constant region of the antibody from which the sequences were derived. A person skilled in the art would readily understand that the variable heavy and light chain sequences of the scFvs disclosed herein may be grafted onto various heavy and light chain constant chains.

Conventional methods can be used to prepare antibodies. For example, by using an ADAM10 or fragment thereof, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (1975) as well as other techniques such as the human B-cell hybridoma technique (Kozbor and Roder, 1983), the EBV-hybridoma technique to produce human monoclonal antibodies (Cole et al., 1985) and screening of combinatorial antibody libraries (Huse et al., 1989). Hybridoma cells can be screened immunochemically for production of antibodies specifically reactive with the peptide and the monoclonal antibodies can be isolated. Therefore, the disclosure also contemplates hybridoma cells secreting monoclonal antibodies with specificity for an ADAM10.

Specific antibodies, or antibody fragments, reactive against an ADAM10 may also be generated by screening expression libraries encoding immunoglobulin genes, or portions thereof, expressed in bacteria with peptides produced from the nucleic acid molecules encoding ADAM10. For example, complete Fab fragments, VH regions and FV regions can be expressed in bacteria using phage expression libraries (See for example Ward et al., 1996, Huse et al., 1989 and McCafferty et al., 1991).

Antibodies may also be prepared using DNA immunization. For example, an expression vector containing a nucleic acid encoding an ADAM10 may be injected into a suitable animal such as mouse. The protein will therefore be expressed in vivo and antibodies will be induced. The antibodies can be isolated and prepared as described above for protein immunization.

The term "heavy chain complementarity determining region" or "heavy chain CDR" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus, for example, as defined by IMGT (Brochet, 2008; Giudicelli, 2011).

The term "light chain complementarity determining region" or "light chain CDR" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus, for example, as defined by IMGT (Brochet, 2008; Giudicelli, 2011).

The disclosure also provides variants of the CDR sequences and antibody or antibody fragment sequences comprising said variant sequences. Such variants include proteins that perform substantially the same function as the specific proteins or fragments disclosed herein in substantially the same way. For example, a functional variant of a CDR or antibody or antibody fragment will be able to bind to an antigen or epitope recognized by the native CDR or antibody or antibody fragment.

Without the intention of being limited thereby, in one embodiment, the substitutions of amino acids are made that preserve the structure responsible for the ability to bind ADAM10. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. Other substitutions might well be possible.

In one embodiment, the variant amino acid sequences of the light chain CDR1, CDR2 and CDR3, and the heavy chain CDR1, CDR2 and CDR3 have at least 50%, at least 60%, at least 70%, at least 80%, at least 90%, at least 95% or at least 98% sequence identity to the CDR sequences disclosed herein.

In another embodiment, the variant amino acid sequences of the single chain variable fragments or antibodies disclosed herein have at least 50%, at least 60%, at least 70%, at least 80%, at least 90%, at least 95% or at least 98% sequence identity to the single chain variable fragment or antibody sequences disclosed herein.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. An optional, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word-length=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search, which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another optional, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

The present disclosure provides immunodetection methods in which an antibody contacts a blood sample suspected of having ADAM10 under conditions and times that allow immune complexes to form. After this time, the sample-antibody composition is washed to remove any non-specific binding and the formed immune complexes are subsequently detected and/or quantified.

In some embodiments, the amount of ADAM10 is quantified, for example, by fluorescence, radioactivity or spectrophotometry depending on the label or marker used. In an embodiment, the amount of ADAM10 is quantified by a radioimmunoassay, an enzyme-linked immunoassay, a competitive binding enzyme-linked immunoassay, dot blot, Western blot, or biolayer interferometry (BLI) or other assays known in the art.

In one embodiment, the probe is in solution. In another embodiment, the probe is immobilized on a solid support or support pad, such as filter paper, a multiwell plate or a microchip.

Detecting the radioactivity, fluorescence or absorbance of a probe may be accomplished by any method known in the art and may be referred to as "signal detection from the probe". In an embodiment, a FACS analyzer or a microplate reader is used. In another embodiment, a suitable detection technology such as a complementary metal-oxide-semiconductor (CMOS) or charge coupled device (CCD) is used and a unique wavelength of light is applied for illumination of the signal.

In one embodiment, detecting the signal from the probe comprises detecting the intensity or quantity of the signal from the probe and is not attributable to background signal.

In some embodiments, the method further comprises testing a series of known reference standards, such as serially diluted samples containing known amounts of ADAM10, optionally, at the same time. The methods optionally further comprise comparing the signal detection of a test subject sample to the signal detection from a reference sample or series of standards of ADAM10 of known quantity.

In one embodiment, the reference sample or control is derived from a reference subject who has suffered a brain injury. In another embodiment, the reference sample or control is derived from a reference subject who has not suffered a brain injury. The reference sample or standards are optionally tested at the same time as the subject blood sample. In another embodiment, the reference sample or standards are tested at different time from the subject blood sample. As used herein, the term "subject blood sample" refers to a blood sample derived from a test subject and the term "subject plasma sample" refers to a plasma sample derived from a test subject.

Correspondence, or similarity, between the signal from a test subject blood sample and the signal from a reference sample from a subject that has suffered a brain injury indicates that the subject has suffered a brain injury. Differences between the signals from the subject sample and the signals from the reference sample from a subject that has suffered a brain injury indicate that the subject has not suffered a brain injury.

Likewise, correspondence, or similarity, between the signal detected from a test subject blood sample and the signal detected from the reference sample from a subject that has not suffered a brain injury indicates that the subject has not suffered a brain injury. Differences between the signal detected from a test subject sample and the signal detected from the reference sample from a subject that has not suffered a brain injury indicates that the subject has suffered a brain injury.

In another embodiment, the identification of an increase in signal detection, optionally a statistically significant increase, of a test subject sample compared to a reference sample from a subject that has not suffered a brain injury indicates that the test subject has suffered a brain injury. In an embodiment, an increase over a cut-off value obtained from historical data from subjects not having suffered a brain injury indicates that the subject has suffered a brain injury.

In another embodiment, the identification of a similar amount of signal detection from a test subject blood sample compared to a reference sample from a subject who has suffered a brain injury or a cut off value obtained from historical data from subjects having suffered a brain injury indicates that the test subject has suffered a brain injury. In one embodiment, a "similar amount" of signal detection refers to no statistically significant difference in signal detection.

In another embodiment, the control is a reference baseline level of ADAM10 of the same test subject. In such an embodiment, the reference baseline level is the level of ADAM10 in the subject prior to the event that is suspected of causing a brain injury. For example, for an athlete, if the reference baseline level of the athlete is available, the post-concussion value may be compared with the off-season reference baseline level. For a soldier, the reference baseline level may be determined prior to any combat.

In a further embodiment, the control is a reference baseline level of a population of athletes during the off-season. The term "off-season" as used herein refers to the time an athlete refrains from actively competing in a sport, for example, for a hockey player, the off-season is typically during the summer months.

In another embodiment, the control is a reference baseline level of the general population. The term "general population" as used herein refers to healthy same age individuals without any history of TBI. In one embodiment, the subject is a child.

In an embodiment, the reference baseline levels disclosed herein may be obtained from historical data that may be updated as further samples are tested.

A reference value in clinical chemistry refers to an average value of an analyte in at least a sample size of 120 healthy individuals. The International Federation of Clinical Chemistry and Laboratory Medicine (IFCC) recommend a sample size of at least 120 to establish reference values for any analyte (Burtis et al, 2012).

Increased signal detection can also be quantified. In one embodiment, at least a 5%, 10%, 25%, 50%, 75% or 100% increase in signal detection from subject samples compared to reference samples from a subject who has not suffered a brain injury or such a cut-off value indicates that the test subject has suffered a brain injury. In another embodiment, at least a 5%, 10%, 25%, 50%, 75% or 100% decrease in signal detection from a test subject blood sample compared to reference sample from a subject who has suffered a brain injury or such a cut-off value indicates that the test subject has not suffered a brain injury.

In another embodiment, samples may be obtained at different time points to detect the progression of the brain injury of a subject. Accordingly there is provided a method of monitoring a subject with a brain injury comprising:
  (i) (a) contacting a blood sample from the subject obtained at a first time point with a probe that binds to ADAM10 and (b) detecting and/or quantifying the amount of ADAM10 at the first time point;
  (ii) (a) contacting a blood sample from the subject obtained at a second time point with a probe that binds to ADAM10 and (b) detecting and/or quantifying the amount of ADAM10 at the second time point; and
  (iii) comparing the amount of ADAM10 from (i) to the amount of ADAM10 from (ii), wherein an increase in the amount of ADAM10 indicates an increase in the severity of the brain injury and a decrease in the amount of ADAM10 indicates an improvement of the brain injury.

In yet another embodiment, there is provided a method of determining whether a subject has suffered a brain injury due to an injury event comprising:
  (i) (a) contacting a blood sample from the subject obtained at a first time point prior to the injury event with a probe that binds to ADAM10;
    (b) detecting and/or quantifying the amount of ADAM10 at the first time point;
  (ii) (a) contacting a blood sample from the subject obtained at a second time point after the injury event, such as 1-6 days after the injury event, with a probe that binds to ADAM10;
    (b) detecting and/or quantifying the amount of ADAM10 at the second time point; and
  (iii) comparing the amount of ADAM10 from the first time point with the amount of ADAM10 at the second time point; wherein an increase in the amount of ADAM10 indicates that the subject has suffered a brain injury due to the injury event.

In one embodiment, the method further comprises obtaining a blood sample from the subject prior to contacting the blood sample with the probe in (i)(a) and/or (ii)(a).

In another embodiment, the first time point provides a baseline level of the subject and the second time point is following the injury event.

In another embodiment, there is provided a method of determining whether a subject has suffered a brain injury due to an injury event comprising:
  (i) (a) contacting a blood sample from a subject after the injury event, optionally obtained 1-6 days after, with a probe that binds to ADAM10;
    (b) detecting and/or quantifying the amount of ADAM10 in (a); and
  (ii) comparing the amount of ADAM10 in (b) with a baseline level of the subject; wherein an increase in the amount of ADAM10 from the baseline level indicates that the subject has suffered a brain injury due to the injury event.

In one embodiment, the baseline level of the subject is a pre-combat level of a subject that may be exposed to combat, or an off-season level of a subject that is an athlete that may be prone to a head injury.

The term "injury event" as used herein refers to any incident that causes trauma or force to the head, including without limitation, an explosion, transportation accident or head injury due to a fall or sports-related event.

In one embodiment, the probe is an antibody or antibody fragment that specifically binds to ADAM10, for example, an antibody or antibody fragment disclosed herein. In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

In some embodiments, the amount of ADAM10 is quantified at each time point, for example, by fluorescence, radioactivity or spectrophotometry depending on the label or marker used. In an embodiment, the amount of ADAM10 is quantified at each time point by a radioimmunoassay, an enzyme-linked immunoassay, a competitive binding enzyme-linked immunoassay, dot blot, Western blot, or biolayer interferometry (BLI) or other assays known in the art.

In some embodiments, the method further comprises testing a series of known reference standards, such as serially diluted samples containing known amounts of ADAM10, optionally, at the same time. The methods optionally further comprise comparing the signal detection of a test subject sample or reference sample to the signal detection from a series of standards of ADAM10 of known quantity in order to quantify the amount of ADAM10.

In one embodiment, the probe at each time point is in solution. In another embodiment, the probe at each time point is immobilized on a solid support or support pad, such as filter paper, a multiwell plate or a microchip.

In another embodiment, two probes may be used in a sandwich ELISA assay. In such an embodiment, the method comprises:
  (a) contacting a blood sample from a test subject with a first probe that binds to ADAM10; and
  (b) contacting the ADAM10 bound to the first probe with a second probe that binds to a different part of the ADAM10; wherein the first or second probe is detectable.

In an embodiment, the first probe is an antibody or fragment thereof that specifically binds to ADAM10 and is immobilized on a solid support and the second probe is an antibody or fragment thereof that specifically binds to ADAM10 at a different epitope than the first probe, is detectable and is in solution. In an alternate embodiment, the first probe is an antibody or fragment thereof that specifically binds to ADAM10, is detectable and is in solution and the second probe is an antibody or fragment thereof that specifically binds to ADAM10 at a different epitope than the first probe and is immobilized on a solid support. In such embodiments, a double antibody-sandwich technique is applied and (b) the amount of ADAM10 in the test subject sample is quantified by comparing to reference standards.

In one embodiment, the probe is an antibody or antibody fragment that binds to ADAM10. Antibodies that bind to ADAM10 are well known in the art. Examples of antibodies that bind to ADAM10 include but are not limited to a polyclonal anti-ADAM10 antibody raised against residues 700 to the C-terminus of human ADAM10 (antibody ab84595, commercially available from Abcam Inc., Toronto, ON, Canada) and a monoclonal antibody against rat ADAM10 (commercially available in an ELISA kit, catalogue number MBS263494, from MyBioSource Inc., San Diego, Calif., USA). In an embodiment, the first and second probes are antibodies or antibody fragments disclosed herein. In an embodiment, the first probe is an antibody or antibody fragment that binds to ADAM10 comprising the heavy chain CDR sequences of SEQ ID NOs: 6, 7 and 8 and/or functional variants thereof and the light chain CDR sequences of SEQ ID NOs: 1, 2 and 3 and/or functional variants thereof and the second probe is an antibody or antibody fragment that binds to ADAM10 comprising the heavy chain CDR sequences of SEQ ID NOs: 6, 7 and 9 and/or functional variants thereof and the light chain CDR sequences of SEQ ID NOs: 1, 2 and 4 and/or functional variants thereof. In another embodiment, the first probe is an antibody or antibody fragment that binds to ADAM10 comprising the amino acid sequence as shown in SEQ ID NO:12 or functional variants thereof or is encoded by the nucleic acid sequence as shown in SEQ ID NO:11 or functional variants thereof and the second probe is an antibody or antibody fragment that binds to ADAM10 comprising the amino acid sequence as shown in SEQ ID NO:14 or functional variants thereof or is encoded by the nucleic acid sequence as shown in SEQ ID NO:13 or functional variants thereof. In yet another embodiment, the first probe is an antibody or antibody fragment that binds to ADAM10 comprising the heavy chain CDR sequences of SEQ ID NOs: 6, 7 and 8 and/or functional variants thereof and the light chain CDR sequences of SEQ ID NOs: 1, 2, and 3 and/or functional variants thereof and the second probe is an antibody or antibody fragment that binds to ADAM10 comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the first probe is an antibody or antibody fragment that binds to ADAM10 comprising the amino acid sequence as shown in SEQ ID NO:12 or functional variants thereof or is encoded by the nucleic acid sequence as shown in SEQ ID NO:11 or functional variants thereof and the second probe is an antibody or antibody fragment that binds to ADAM10 comprising the amino acid sequence as shown in SEQ ID NO:16 or functional variants thereof or is encoded by the nucleic acid sequence as shown in SEQ ID NO:15 or functional variants thereof, or vice versa. In yet a further embodiment, the first probe is an antibody or antibody fragment that binds to ADAM10 comprising the heavy chain CDR sequences of SEQ ID NOs: 6, 7 and 9 and/or functional variants thereof and the light chain CDR sequences of SEQ ID NOs: 1, 2, and 4 and/or functional variants thereof and the second probe is an antibody or antibody fragment that binds to ADAM10 comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the first probe is an antibody or antibody fragment that binds to ADAM10 comprising the amino acid sequence as shown in SEQ ID NO:14 or functional variants thereof or is encoded by the nucleic acid sequence as shown in SEQ ID NO:13 or functional variants thereof and the second probe is an antibody or antibody fragment that binds to ADAM10 comprising the amino acid sequence as shown in SEQ ID NO:16 or functional variants thereof or is encoded by the nucleic acid sequence as shown in SEQ ID NO:15 or functional variants thereof, or vice versa.

In one embodiment, the detectable probe comprises an enzyme and enzymatic activity can be used to detect and quantify the amount of ADAM10. For example, the antibody or antibody fragment thereof can be conjugated to biotin and complexed with the biotin-binding-protein avidin conjugated to the enzyme horse radish peroxidase (HRP). HRP activity can be exposed to the substrate TMB to yield a blue colour which, upon adding stop solution turns to yellow, the intensity of which is indicative of the amount of activity of the enzyme and can be measured by spectrophotometry at an absorbance of 450 nm.

Other examples of detectable probes are well known in the art. For example, in one embodiment, the detectable probe comprises biotin conjugated to the antibody or antibody fragment. Avidin and/or streptavidin, which both bind biotin, can then be used to amplify the detectable signal. Avidin and/or streptavidin can be labelled with reporters including, but not limited to, horse radish peroxidase (HRP) which can hydrolyze 3,3',5,5'-tetramethylbenzidine (TMB), alkaline phosphatase (ALP) which can hydrolyze p-nitrophenyl phosphate (PNPP), beta galactosidase (β-gal) which can hydrolyze 2-nitrophenyl β-D-galactopyranoside (ONPG), and beta lactamase (β-lac) which can hydrolyze ampicillin. The reaction product can be read at specific wavelengths (typically between 400-500 nm). Specific wavelength values are normally provided by the manufacturer or can be determined by a person of skill in the art.

The methods disclosed herein optionally further comprise treating the test subject for the brain injury or selecting therapy for brain injury if the amount of ADAM10 is increased compared to a reference sample from a subject not having a brain injury.

For example, patients suffering from brain injury may be treated based on their neurologic status and findings on a CT scan. Large epidural hematomas (>30 ml in volume) and subdural hematomas >10 mm in thickness or associated with more than 5 mm in midline shift may be treated with surgical evacuation. Patients with epidural hematomas and a Glasgow Coma Scale (GCS) ≤8 who have pupillary abnormalities and patients with subdural hematomas who have a GCS score ≤8 or whose GCS score has decreased by ≥2 points from the time of admission may also be treated with surgery. Evacuation of an intracranial hemorrhage may be recommended if it is in the posterior fossa. Open skull fractures and depressed skull fractures, with displacement more than the thickness of the cranium, may also be treated surgically. A course of prophylactic anti-epileptic treatment may be recommended in patients with brain hematomas. The Glasgow Coma Scale measures the level of consciousness in a person following a brain injury.

Accordingly, in another embodiment, the method further comprises treating the subject with surgery, such as surgical evacuation, if a brain injury is detected. In another embodiment, the method further comprises treating the subject with anti-epilepsy drugs if a brain injury is detected.

Having a non-expensive and easy to use diagnostic kit will be a very useful tool to screen victims particularly those with no visible physical signs by the first responders (paramedics, nurses, and doctors) or in clinics and facilities with no CT scan. Considering the fact that in the blast-induced TBI (those who experience the blast force far from epicenter) and sport-related concussions, victims with no apparent physical wound may be ignored or misrepresented, this kit would assist to screen and find invisible victims for further observation/test and treatment. The methods and kits disclosed herein can be used as a supportive tool for more comprehensive CT scan imaging as well.

The present disclosure also provides kits for analyzing blood to detect a brain injury.

In one embodiment, the kit comprises:
(a) a probe that detects the presence or amount of ADAM10 in the blood; and
(b) instructions for use in detecting brain injury.

In one embodiment, the instructions for use provide instructions on how to perform any of the methods described herein. In another embodiment, the instructions for use provide instruction on further treatment options depending on presence or amount of ADAM10.

In one embodiment, the probe is an antibody or antibody fragment that specifically binds to ADAM10, for example, an antibody or antibody fragment disclosed herein.

In another embodiment, the kit comprises two probes, an immobilized probe that binds to ADAM10 at a first position and a detectable probe that binds to ADAM10 at a second position. In an embodiment, the probe that binds to ADAM10 at a first position is an antibody or antibody fragment comprising the heavy chain CDR sequences of SEQ ID NOs: 6, 7 and 8 and/or functional variants thereof and the light chain CDR sequences of SEQ ID NOs: 1, 2 and 3 and/or functional variants thereof and the probe that binds to ADAM10 at the second position is an antibody or antibody fragment comprising the heavy chain CDR sequences of SEQ ID NOs: 6, 7 and 9 and/or functional variants thereof and the light chain CDR sequences of SEQ ID NOs: 1, 2 and 4 and/or functional variants thereof; or vice-versa. In another embodiment, the probe that binds to ADAM10 at a first position comprises the amino acid sequence as shown in SEQ ID NO:12 or functional variants thereof or is encoded by the nucleic acid sequence as shown in SEQ ID NO:11 or functional variants thereof and the probe that binds to ADAM10 at the second position is an antibody or antibody fragment that binds to ADAM10 comprising the amino acid sequence as shown in SEQ ID NO:14 or functional variants thereof or is encoded by the nucleic acid sequence as shown in SEQ ID NO:13 or functional variants thereof, or vice versa. In yet another embodiment, the probe that binds to ADAM10 at a first position is an antibody or antibody fragment comprising the heavy chain CDR sequences of SEQ ID NOs: 6, 7 and 8 and/or functional variants thereof and the light chain CDR sequences of SEQ ID NOs: 1, 2, and 3 and/or functional variants thereof and the probe that binds to ADAM10 at a second position is an antibody or antibody fragment comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the probe that binds to ADAM10 at a first position comprises the amino acid sequence as shown in SEQ ID NO:12 or functional variants thereof or is encoded by the nucleic acid sequence as shown in SEQ ID NO:11 or functional variants thereof and the probe that binds to ADAM10 at a second position comprises the amino acid sequence as shown in SEQ ID NO:16 or functional variants thereof or is encoded by the nucleic acid sequence as shown in SEQ ID NO:15 or functional variants thereof, or vice versa. In yet a further embodiment, the probe that binds to ADAM10 at a first position is an antibody or antibody fragment comprising the heavy chain CDR sequences of SEQ ID NOs: 6, 7 and 9 and/or functional variants thereof and the light chain CDR sequences of SEQ ID NOs: 1, 2, and 4 and/or functional variants thereof and the probe that binds to ADAM10 at a second position is an antibody or antibody fragment comprising the heavy chain CDR sequences of SEQ ID NOs: 6, 7 and 10 and/or functional variants thereof and the light chain CDR sequences of SEQ ID NOs: 1, 2 and 5 and/or functional variants thereof, or vice versa. In another embodiment, the probe that binds to ADAM10 at a first position comprises the amino acid sequence as shown in SEQ ID NO:14 or functional variants thereof or is encoded by the nucleic acid sequence as shown in SEQ ID NO:13 or functional variants thereof and the probe that binds to ADAM10 at a second position comprises the amino acid sequence as shown in SEQ ID NO:16 or functional variants thereof or is encoded by the nucleic acid sequence as shown in SEQ ID NO:15 or functional variants thereof, or vice versa.

In one embodiment, the probe comprises a marker or label for detection, such as a radioactive, fluorescent, biological or enzymatic label. In an alternative embodiment, a secondary binding ligand is used, such as a second antibody or biotin/avidin ligand binding agent, as is known in the art for detection of the probe.

In one embodiment, the kit further comprises serially diluted samples of ADAM10 to be used as standards for quantifying the amount of ADAM10.

In some embodiments, the amount of ADAM10 is quantified, for example, by fluorescence, radioactivity or spectrophotometry depending on the label or marker used and the kit comprises reagents for such detection. In an embodiment, the amount of ADAM10 is quantified by a radioimmunoassay, an enzyme-linked immunoassay, a competitive binding enzyme-linked immunoassay, dot blot, or Western blot, biolayer interferometry (BLI) or other assays known in the art and the kit comprises reagents for such assays, for example, the kit may comprise Ellman's reagent when the label is the enzyme acetylcholinesterase or TMB (3,3',5,5'-tetramethylbenzidine) substrate when the label is the enzyme horse radish peroxidase.

In one embodiment, the probe is in solution. In another embodiment, the probe is immobilized on a solid support or support pad, such as filter paper, a multiwell plate or a microchip.

The present disclosure further provides a use of ADAM10 in a blood sample as a biomarker to detect a brain injury. Also provided herein is use of a probe disclosed herein that binds to ADAM10 in a blood sample to detect a brain injury. In an embodiment the brain injury is a traumatic brain injury. In a further embodiment the blood sample is plasma or serum.

The methods, uses, and kits disclosed herein can be used in conjunction with other tools that diagnose brain injuries, including CT scan imaging and magnetic resonance imaging (MRI).

Antibodies and Antibody Fragments

The present disclosure also provides novel antibodies and antibody fragments that bind to ADAM10 protein.

Accordingly, in one embodiment, there is provided an antibody or antibody fragment that binds to ADAM10 comprising the heavy chain CDR sequences of SEQ ID NOs: 6, 7 and 8 and/or functional variants thereof and the light chain CDR sequences of SEQ ID NOs: 1, 2 and 3 and/or functional variants thereof.

In another embodiment, there is provided an antibody or antibody fragment that binds to ADAM10 comprising the heavy chain CDR sequences of SEQ ID NOs: 6, 7 and 9 and/or functional variants thereof and the light chain CDR sequences of SEQ ID NOs: 1, 2 and 4 and/or functional variants thereof.

In yet another embodiment, there is provided an antibody or antibody fragment that binds to ADAM10 comprising the heavy chain CDR sequences of SEQ ID NOs: 6, 7 and 10 and/or functional variants thereof and the light chain CDR sequences of SEQ ID NOs: 1, 2 and 5 and/or functional variants thereof.

In a further embodiment, there is provided an antibody or antibody fragment that binds to ADAM10 comprising the amino acid sequence as shown in SEQ ID NO:12 or a functional variant thereof or is encoded by the nucleic acid sequence as shown in SEQ ID NO:11 or a functional variant thereof.

In another embodiment, there is provided an antibody or antibody fragment that binds to ADAM10 comprising the amino acid sequence as shown in SEQ ID NO:14 or a functional variant thereof or is encoded by the nucleic acid sequence as shown in SEQ ID NO:13 or a functional variant thereof.

In yet a further embodiment, there is an antibody or antibody fragment that binds to ADAM10 comprising the amino acid sequence as shown in SEQ ID NO:16 or a functional variant thereof or is encoded by the nucleic acid sequence as shown in SEQ ID NO:15 or a functional variant thereof.

In one embodiment, the antibody fragment is a Fab, Fab', F(ab')2, Fv or scFv. In a particular embodiment, the antibody fragment is a single chain variable fragment (scFv).

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: Rat Model

Blast-mTBI animal studies were conducted as previously described (Yarnell et al 2013 and Pham et al 2015 a). Briefly, adult male Sprague Dawley (SD) rats (375-400 g) were anesthetized with 3% isoflurane in 100% oxygen before being securely placed within a helium driven blast tube. The rats are positioned within the tube in such a way as to allow head-only lateral exposure to a blast along the length of the blast tube. The head of the animal is securely restrained atop a small platform by mesh netting (restraint condition) or is not restrained (whiplash condition). Helium gas pressure is built up within a pressure driver section that is divided from the blast tube by a plastic acetate sheet barrier. Depending on the thickness of the plastic acetate sheet barrier, a single primary blast overpressure wave of 15, 20, 25, or 30 pounds per square inch (PSI) (103.4-206.8 kilopascals (kPa)) is produced that bursts through the acetate divider and travels along the blast tube to impact the anesthetized animal along the side of the head. Reflective blast waves are prevented by an end wave eliminator device at the distal end of the blast tube to ensure single blast pulse exposure only. Anesthetized sham blast exposure trials (0 PSI) were also performed. Following blast exposure, animals were removed from the blast tube and allowed to recover before being returned to an animal holding facility. 24 hours after the blast or sham experiments, animals were decapitated and exsanguinated. Small blood samples were collected in potassium ethylene diamine tetra-acetic acid coated tubes (BD Vacutainer K2EDTA #367841) and then centrifuged for 10 minutes at 2000 g. The plasma separated fraction was aliquoted into 1.5 mL Eppendorf® tubes and stored at −80'C until use for western blotting and ELISA assays for ADAM10. Samples from all conditions (0, 15, 20, 25, and 30 PSI) were evaluated by Western blotting. Control samples (0 PSI) and samples from the lowest magnitude of blast force (15 PSI) were further evaluated by ELISA for the restraint condition.

Western blotting was carried out using a conventional Western blotting method on PVDF membrane using a commercially available rabbit polyclonal anti-ADAM10 antibody (Abcam Inc, Toronto, ON, Canada, catalogue #ab84595) as described by the supplier. Briefly, the protein concentration of ADAM10 in plasma samples was determined using the Bio-Rad DC assay and 30 μg total protein per well was loaded into 15% acrylamide gels for SDS-PAGE. Protein was then transferred onto PVDF membrane (FluoroTrans, Pall Life Sciences) at 100V for 1 hour. Membranes were blocked in 5% bovine serum albumin in PBS-Tween 20 (0.1%) at room temperature (RT) for 1 hour. Primary antibodies used for immunoblotting targeted ADAM10 (Abcam, 1:1000), and actin (Santa Cruz sc-1616, 1:500). Primary antibody incubation was performed either at room temperature for 1-2 hours or at 4° C. overnight. Following stringent washing and secondary antibody incubation steps, membranes were exposed to enhanced chemiluminescence reagent (Amersham) and exposed to x-ray film. ADAM10 bands were analyzed using NIH ImageJ software and normalized to that of the actin loading control in each sample lane.

ELISAs were carried out using a commercially available ADAM10 ELISA kit (MyBiosource Inc., San Diego, Calif., USA, catalogue no. MBS263494) using the following protocol. 100 μl of serially diluted protein standards (5000-78 pg/mL) and diluted plasma samples (10-15×) were added to pre-designated wells in triplicate. The reaction plate was sealed with an adhesive plastic cover and incubated at 37° C. for 60 min. The well contents were then discarded and the reaction plate was washed three times with 200 μl of phosphate buffered saline (PBS) per well. The plate was then inverted and blotted dry on tissue paper. Next, 100 μl of biotinylated Adam10 antibody solution was added to each well. The reaction plate was next sealed and incubated at 37° C. for 60 min. After incubation, the plate contents were discarded and the plate was washed three times with PBS. The plate was then inverted and blotted dry on tissue paper. Next, avidin-HRP solution was added to each well (100 μl per well, except blanks). The reaction plate was then sealed and incubated at 37° C. for 30 min. After incubation, the plate contents were discarded and the plate was washed five times, inverted, and blotted dry with tissue paper. Next, 100 μl of TMB substrate solution was added to each well. The plate was then sealed and incubated in the dark at 37° C. for up to 30 min while being observed for blue color development. Once a color gradient had developed within the protein standards well, 100 μl of stop solution was added to each well and the wells were observed for yellow colour development. The plate was mixed gently and absorbance was read at OD 450 nm within 10 minutes of adding the stop solution.

Results:

Restraint Condition

Figure 2:
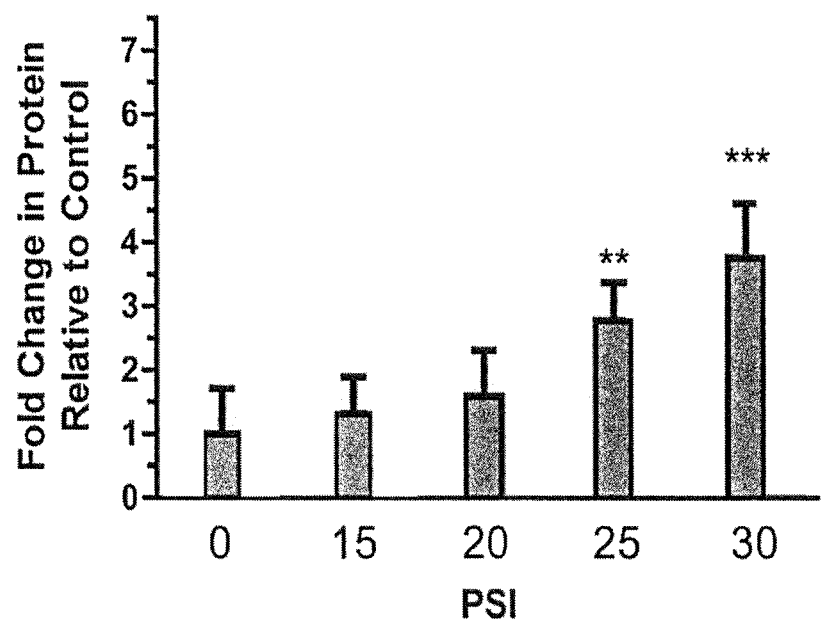
FIG. 2 depicts a numerical (fold) change bar graph representing a mean fold increase in the amount of ADAM10 in serum samples from rats exposed to a 15, 20, 25, or 30 PSI blast in the restraint condition relative to serum samples from control rats not exposed to blast (0 PSI).

ADAM10 levels were determined semi-quantitatively using Western blotting. One-way ANOVA found that mean IR of ADAM10 in blast exposed groups was significantly different (p<0.001) relative to control. Post-hoc Dunnett's multiple comparison of blast groups against control for ADAM10 IR are as follows: 0 PSI (n=5, mean 1.00±0.71 fold), 15 PSI (n=4, mean 1.32±0.57 fold), 20 PSI (n=4, mean 1.59±0.72 fold), 25 PSI (n=4, mean 2.79±0.59 fold; p<0.01), and 30 PSI (n=4, mean 3.77±0.85 fold (p<0.001) as shown in FIGS. 1 and 2. The plasma ADAM10 levels were steadily increased in animals treated under the restraint condition as the magnitude of blast forces raised and there appears to be a correlation between blast magnitude and increasing levels of plasma ADAM10, as shown in FIG. 2.

ADAM10 levels in 0 PSI and 15 PSI serum samples (restraint condition) were analyzed by ELISA. The 15 PSI samples had a 3-fold increase in ADAM10 levels compared to control samples (see FIG. 5).

Whiplash Condition

Figure 3:
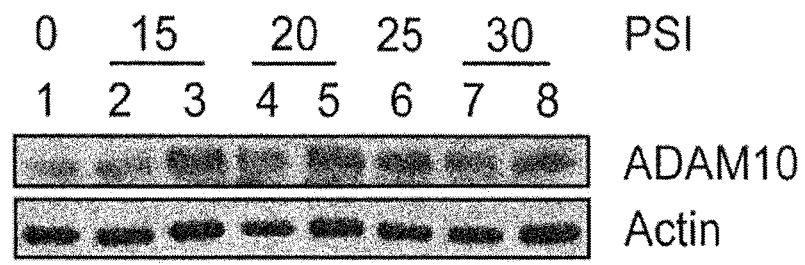
FIG. 3 shows a Western blot of ADAM10 compared to an actin control. Results are semi-quantitative and are for the purpose of simple visualization of an increased amount of ADAM10 in serum samples from rats exposed to a 15, 20, 25, or 30 PSI blast in the whiplash condition relative to serum samples from control rats not exposed to blast (0 PSI).
Figure 4:
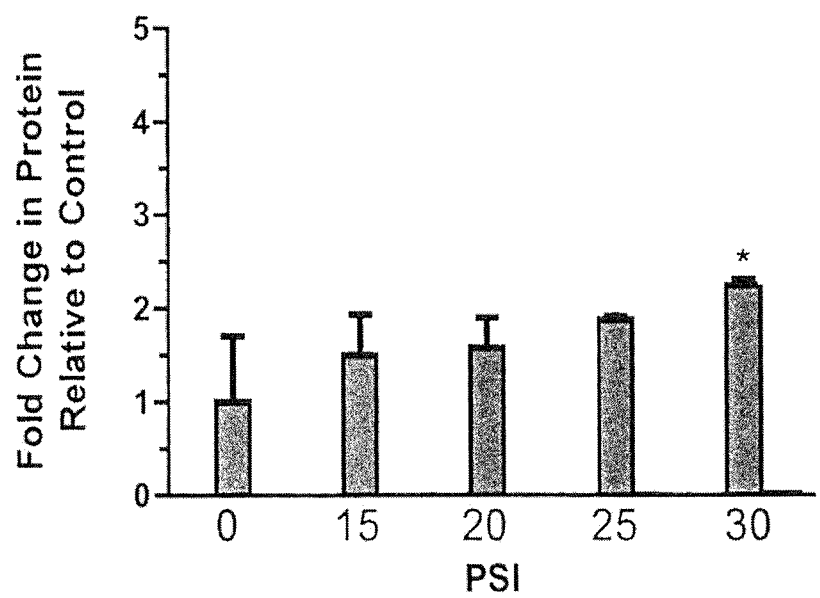
FIG. 4 depicts a numerical (fold) change bar graph representing a mean fold increase in the amount of ADAM10 in serum samples from rats exposed to a 15, 20, 25, or 30 PSI blast in the whiplash condition relative to serum samples from control rats not exposed to blast (0 PSI).

One-way ANOVA found that mean IR was not significant for ADAM10 (p>0.05). Post-hoc Dunnett's multiple comparison of blast groups against control for ADAM10 IR are as follows: 0 PSI (n=5, mean 1.00±0.71 fold), 15 PSI (n=2, mean 1.51±0.43 fold), 20 PSI (n=3, mean 1.59±0.32 fold), 25 PSI (n=3, mean 1.89±0.04 fold), and 30 PSI (n=3, mean 2.25±0.07 fold; p<0.05) as shown in FIGS. 3 and 4. Plasma ADAM10 levels appeared to increase as the magnitude of blast forces raised, but this increase did not reach the level of statistical significance until the 30 PSI time point, as shown in FIG. 4.

Discussion

A Disintegrin and metalloproteinase domain-containing protein 10 (ADAM10) levels increased significantly in plasma samples of blast-exposed rats under two different experimental conditions, restraint and whiplash, when compared with control non-blast-exposed rats. There appears to be a correlation between blast magnitude and increasing plasma levels of plasma ADAM10. ADAM10 is a conserved cell-membrane-localized enzyme with a length of 748 aa and is a member of ADAM metalloproteinases family. In addition to the plasma membrane (PM), ADAM10 is predominantly expressed in the Golgi apparatus. It is also detectable in released membrane vesicles. ADAM10 is primarily known for its function as an α-secretase in cleaving amyloid precursor protein (APP). ADAM10 is involved in a variety of biological functions, and has been implicated in the pathogenesis of diseases ranging from cancer to Alzheimer Disease (AD) (Vingtdeux and Marambaud, 2012; Endres and Fahrenholz, 2012). The α-secretase activity of ADAM10 prevents formation of toxic APP fragments and boosts production of neurotrophic and neuroprotective APP related fragments. ADAMs are type I transmembrane zinc proteinases and ADAM10 is the major ADAM sheddase involved in regulated intramembrane proteolysis with a very important role in Notch/Delta signaling, APP processing and PrPc shedding. In fact, lack of ADAM10 leads to intracellular accumulation and loss of shedding of the cellular prion protein in vivo (Altmeppen et al, 2011). Most recently an elevation in mRNA and protein expression of ADAM10 has been reported in rat brain (hippocampus) following TBI (Warren et al, 2012). In another study, Zohar et al 2011 reported promising cognition improvement in an animal model of TBI following administration of the PKC activator bryostatin1. It has been hypothesized that the protection offered by bryostatin1 may be mediated by ADAM10 activation and by deactivation of a β-secretase BACE1 (Zohar et al, 2011).

It is not yet known how ADAM10 reaches into the peripheral circulation from the CNS after a TBI event. While not wishing to be bound by theory, the present inventors hypothesized that exosomes containing ADAM10 may partly contribute to its circulation appearance. ADAM10 has been previously identified in neuronal exosomes (Sharples et al, 2008). Exosomes are endosomal origin small-membrane vesicles with a size of 30-120 nm in diameter containing functional mRNAs and micro-RNAs (miRNAs) as well as proteins and there is some evidence that exosomes may pass through the blood brain barrier (BBB) (Mathivanan et al 2010; van der Pol et al, 2012). Without wishing to be bound by theory, the present inventors hypothesized that when an amount of force applied on the brain is of sufficient magnitude to cause a concussion or mTBI, the force may lead to the activation and release of ADAM10, possibly in exosomes, from the central nervous system (CNS) into the circulation where it subsequently accumulates within the systemic circulation.

Example 2: Athletes

Members of University of Saskatchewan Huskies Athletic teams including Canadian football, ice hockey, basketball, and soccer teams as well as healthy non-athlete male and female university students were asked to participate in this investigation. Individuals were asked in a questionnaire whether they were in good-standing health without any existing illnesses or conditions and whether they had recently (<6 months) suffered a head injury. Those who had a pre-existing condition or had suffered a recent injury were excluded from the study to prevent potential confounds. In total, 103 participants submitted a blood sample. Initial samples submitted by some athletes before the pre-season training are treated as baselines, and should an athlete suffer a significant head injury throughout the season a subsequent post-TBI sample was collected. For this study plasma samples were collected from 4 concussed athletes who were identified during the season using the sports concussion assessment tool (SCAT)3 concussion assessment criteria (Guskiewicz et al, 2013) and their post-concussion blood samples were collected 1-6 days post-injury event depending on the subject's availability. Descriptions of the athletes' injuries are provided in Table 1. Randomly selected age and gender matched blood samples from healthy control subjects were used as controls for comparison with concussed athlete plasma specimens (Pham et al. 2015 b).

Figure 5:
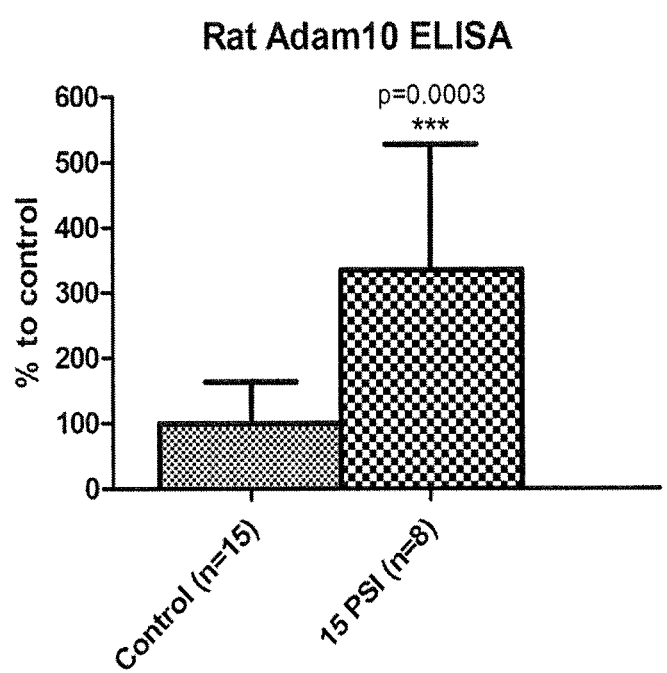
FIG. 5 depicts a percentage of increase in plasma ADAM-10 in rats exposed to 15 PSI blast (restraint) compared to that in control rats (sham control) using a quantitative ELISA test.
Figure 6:
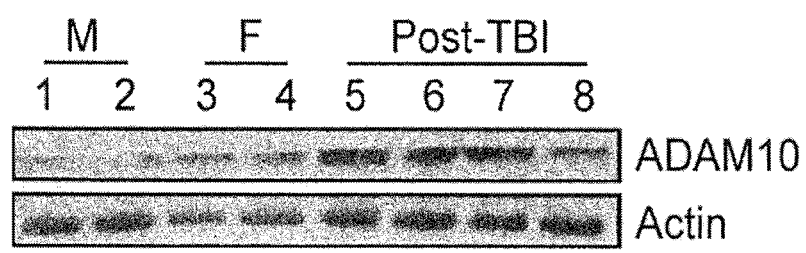
FIG. 6 shows a Western blot of ADAM10 compared to an actin control. Results are semi-quantitative and are for the purpose of simple visualization of an increased amount of ADAM10 in serum samples from athletes post-TBI compared to serum samples from randomly selected age and sex matched control individuals.
Figure 7:
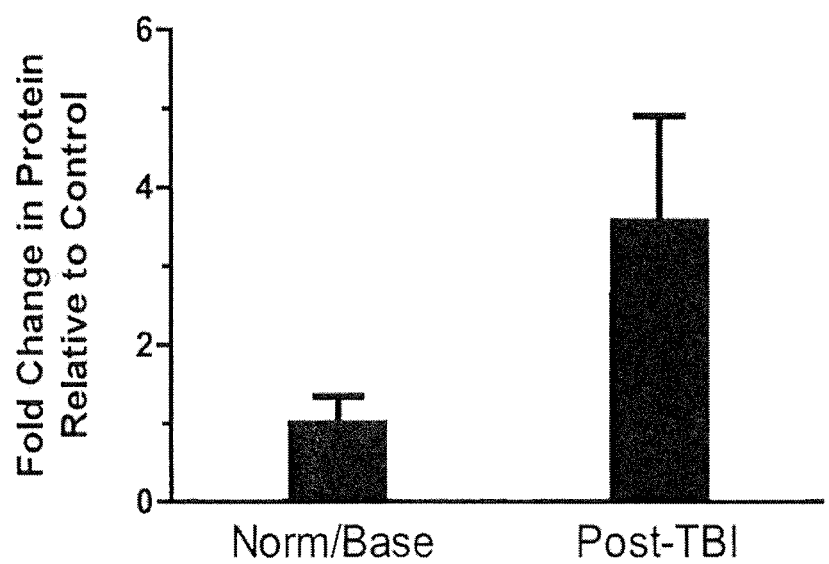
FIG. 7 depicts a numerical (fold) change bar graph representing a mean fold increase in the amount of ADAM10 in serum samples from athletes post-TBI compared to serum samples from randomly selected age and sex matched control individuals.

Results:

ADAM10 also showed an increase in concussed athletes' plasma samples (n=4 mean 3.57±1.34 fold), but this increase was not significant in comparison to the control/baseline (see FIGS. 5 and 6). The low number of concussed athletes evaluated and variability in the timing of post-concussion blood sampling most likely contributed to not reaching significant levels, although a striking elevation of plasma ADAM10 levels was observed after TBI.

Discussion

Plasma ADAM10 levels in concussive athletes increased more than 3.5 times that in randomly selected age and sex matched controls. Due likely to the small number of concussions in this study (n=4) this result did not fall within significant limits, but was close to significant. Despite the small sample size, this pilot study indicates that plasma ADAM10 may be used as a biomarker for TBI, either alone or in conjunction with one or more additional known TBI markers such as GFAP, UCLH, or S100B.

Example 3: Novel Single Chain Variable Fragments that Bind ADAM-10

Results:
Generation of scFv Antibody Fragments Binding Human ADAM10

A synthetic human IgG1 scFv library was created containing over $10^{10}$ unique single-chain variable fragment (scFv) antibodies fused to the PIII coat protein of M13 filamentous phage. Phage-display selections were then used to select scFvs that bind purified human ADAM10. Following an iterative screening process to enrich for ADAM10 binders, three unique scFv clones were recovered and the complete DNA coding sequence was identified (Table of Sequences). Table 2 shows the antigen binding sequences of each antibody fragment. Regarding the overall antibody framework sequence that flanks the CDRs: the light chain most closely aligns to the human IgKV1-16 germline gene and the heavy chain most closely aligns to the human IgHV3-30 germline gene.

Binding of scFv Antibody Fragments to ADAM10 by Phage ELISA

A phage-based ELISA was performed as a semi-quantitative approach to initially validate scFv binding to ADAM10. ADAM10 was adsorbed to ELISA plates and purified phage displaying each of the scFv clones was tested for a binding signal compared to a negative control bovine serum albumin (BSA) protein. Strong binding signals were observed with the average binding signal against ADAM10 target over BSA calculated as 45.7, 37.1, and 42.1 for scFv-B2,-B7, and -B9, respectively (Table 3).

Production of Purified scFv Antibody Fragments

Figure 8:
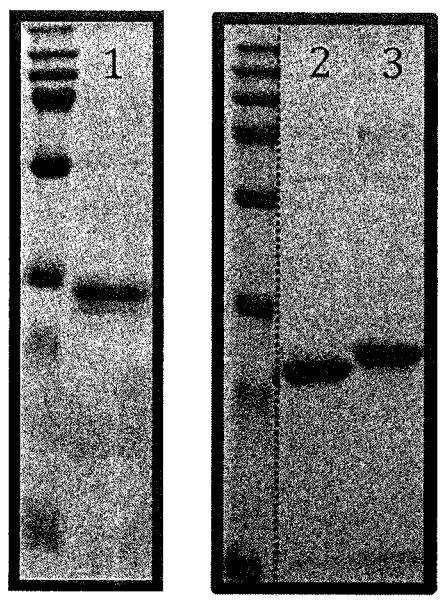
FIG. 8 shows an SDS-PAGE of purified scFv antibody fragments. SDS-PAGE gels with samples of purified scFv-B2 (1), scFv-B7 (2), scFv-B9 (3) were used to evaluate purity and provide a visual indication of protein quality. The dotted line indicates the removal of irrelevant samples from the same gel image.

The scFv coding sequences were sub-cloned into a bacterial expression vector to express scFv protein in *Echerichia coli*. An automated affinity chromatography purification protocol was then employed to purify scFvs from bacteria culture lysates. High soluble yields (Table 4) indicated that the scFvs fold well and are well tolerated in *E. coli*, and a single prominent band with purity to near homogeneity was observed in SDS-PAGE (FIG. 8).

Figure 9:
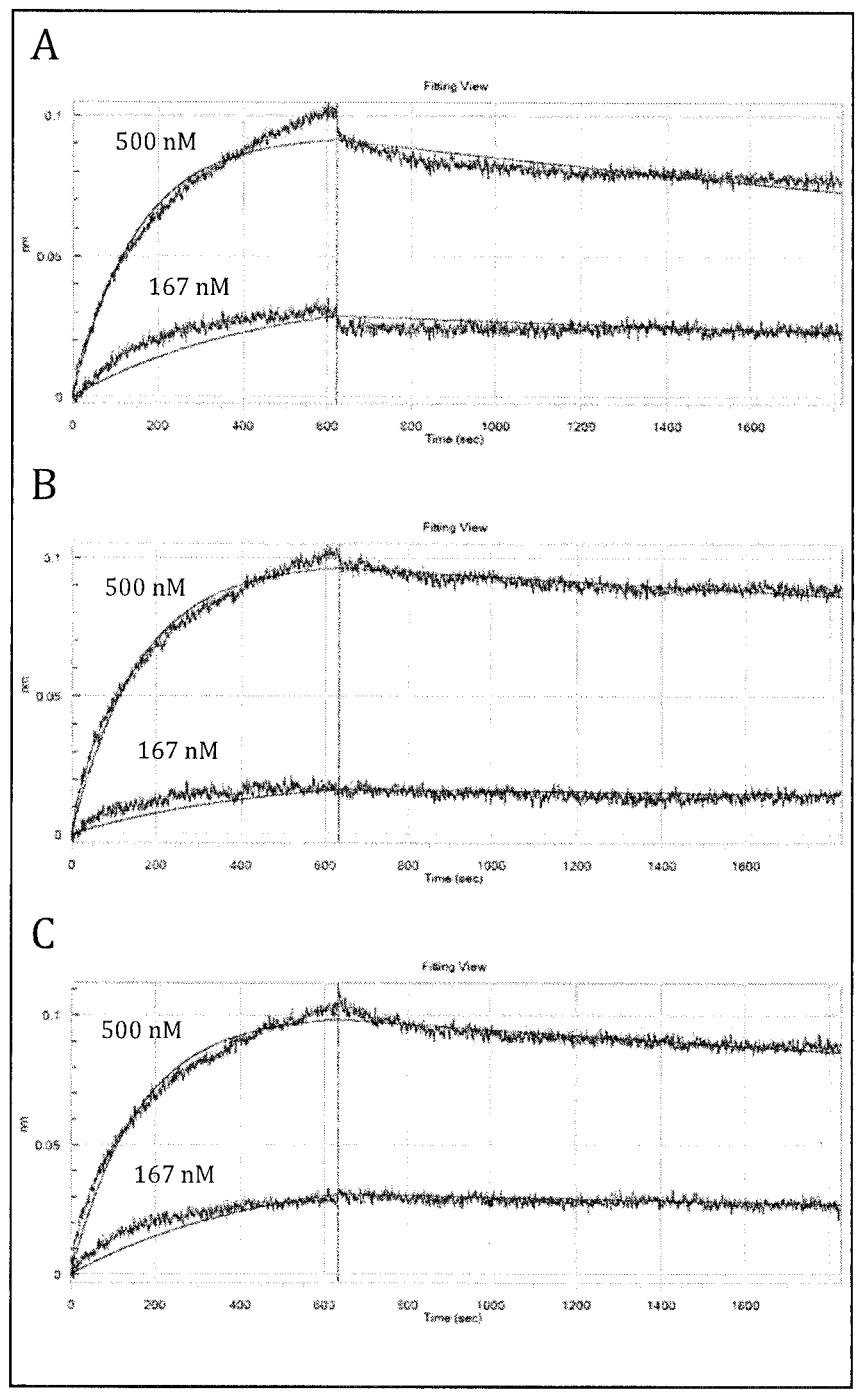
FIG. 9 shows kinetic analysis of ADAM10-binding antibody fragments by biolayer interferometry. BLI sensorgrams for scFv-B2 (A), scFv-B7 (B), and scFv-B9 (C) show real-time binding curves in nanometers of optical thickness versus time (sec). The area to the left of the dotted line shows association to ADAM10 at the indicated concentrations (nM), and the dissociation phase in buffer alone is to the right. A global best fit (solid red line) for each curve was calculated by ForteBio Data Anaylsis 7.1 software and used to determine the kinetic parameters in Table 5.

Kinetic Analysis of Purified scFv Antibody Fragment Binding to ADAM10 by Biolayer Interferometry To better characterize binding to ADAM10, biolayer interferometry (BLI) was used to generate a binding signal to confirm that the purified scFvs can bind free ADAM10 in solution, as compared with the plate-adsorbed ADAM10 in the ELISA assays above. A more complete BLI experiment was then used to quantify the binding kinetics of the interaction between ADAM10 and the scFv antibodies. FIG. 9 shows the ADAM10 binding and dissociation curves for each of the scFvs from which curve-fitting software was used to calculate the kinetic values in Table 5.

Kinetic Analysis of Biotin-Labeled scFv Antibody Fragments

Figure 10:
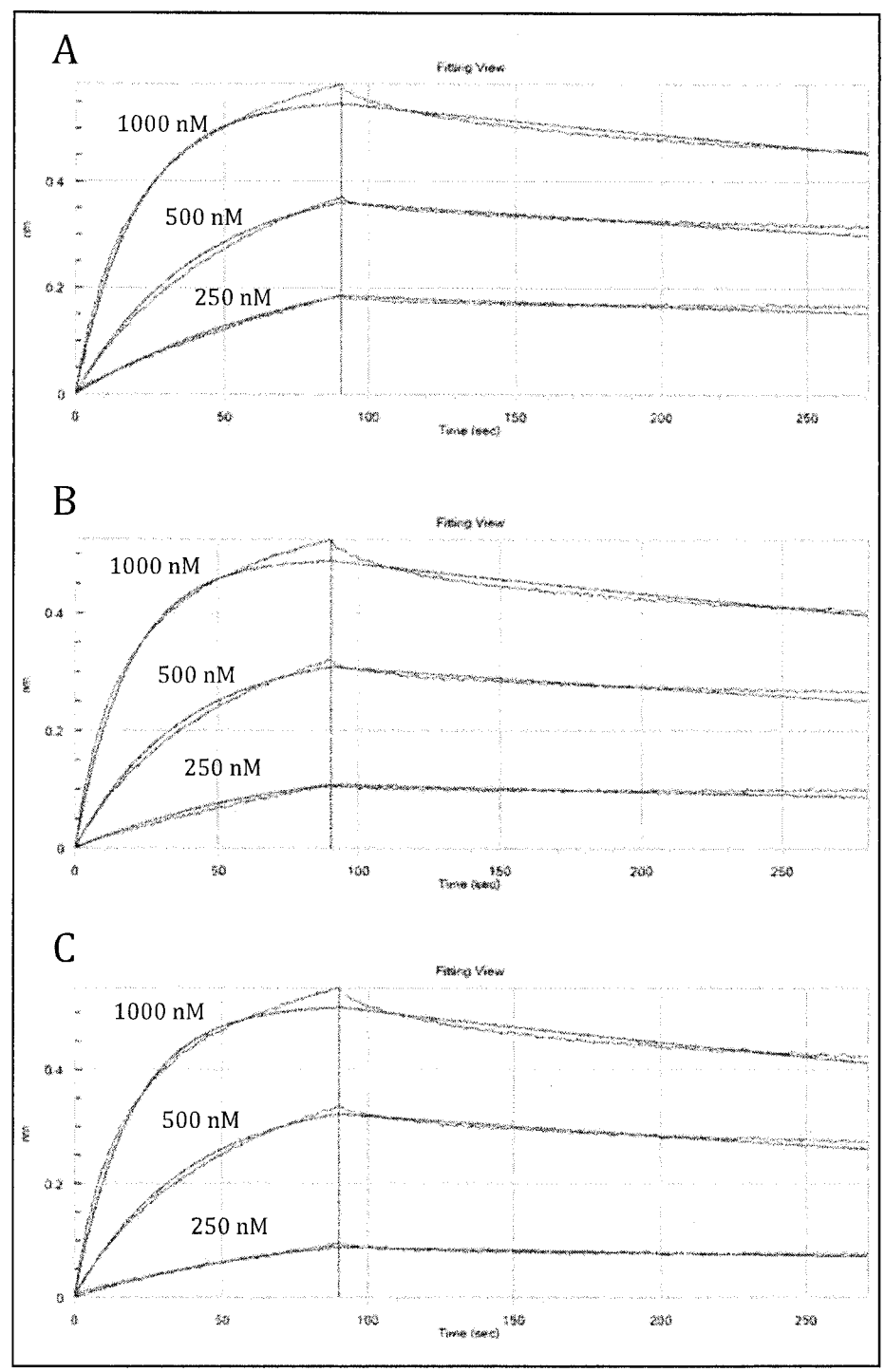
FIG. 10 shows kinetic analysis of biotin-labeled scFv antibody fragments by biolayer interferometry. BLI sensorgrams for biotin-scFv-B2 (A), biotin-scFv-B7 (B), and biotin-scFv-B9 (C) show real-time binding curves in nanometers of optical thickness versus time (sec). The area to the left of the dotted line shows association to ADAM10 at the indicated concentrations (nM), and the dissociation phase in buffer alone is to the right. A global best fit (solid red line) for each curve was calculated by ForteBio Data Anaylsis 7.1 software and used to determine the kinetic parameters in Table 6.

With the goal to develop a sandwich-based diagnostic assay that would use labeled and unlabeled scFv components, each of the antibody fragments was next covalently labeled with biotin in an amine-coupling reaction. A kinetic BLI experiment was then performed to confirm that the biotin-labeled scFv antibody fragments retain binding to ADAM10 (FIG. 10 and Table 6). In this analysis, the $K_D$ for all interactions was found to be in the low nanomolar range as seen with the unlabeled scFvs (Table 5); however, the rate of dissociation ($k_{dis}$) was increased by an order of magnitude (eg. $1.17 \times 10^3$ for biotin-labeled scFv-B9 compared with $1.15 \times 10^{-4}$ for the corresponding unlabeled scFv). This may be due in part to the fitting of the dissociation curve in FIG. 9, which fits an off-rate that is clearly over-represented. Despite this, the differing kinetics could be conformational because the biotin-conjugated scFvs were immobilized with streptavidin biosensors, and not direct amine-reactive biosensors as for the unlabeled antibody fragments.

Figure 11:
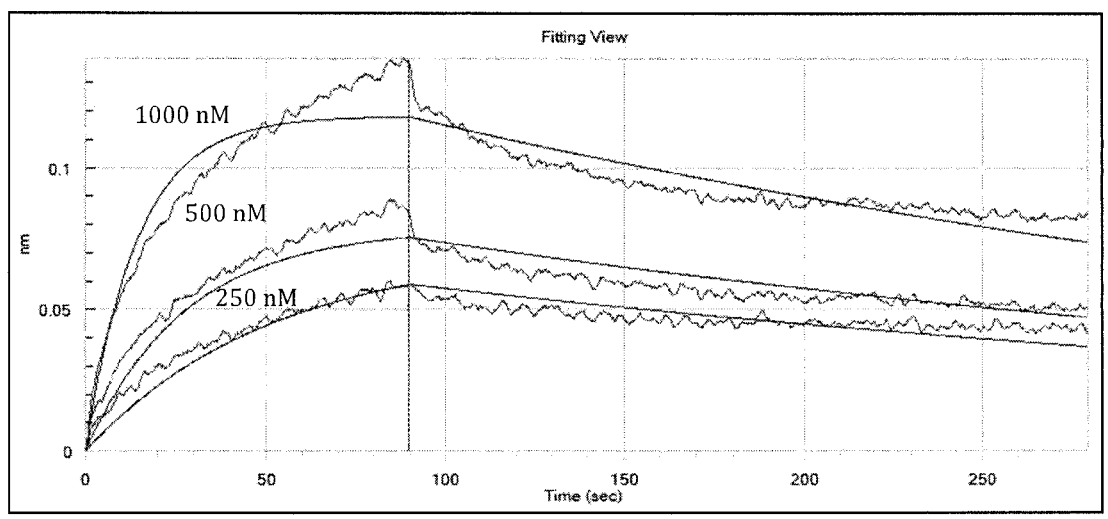
FIG. 11 shows kinetic analysis of commercial biotin-labeled antibody by biolayer interferometry. BLI sensorgram of the interaction between a Biomatik antibody and ADAM10 is shown by a real-time binding curve in nanometers of optical thickness versus time (sec). The area to the left of the dotted line shows association to ADAM10 at the indicated concentrations (nM), and the dissociation phase in buffer alone is to the right. A global best fit (solid red line) for each curve was calculated by ForteBio Data Anaylsis 7.1 software and used to determine the kinetic parameters in Table 7.

Biolayer Interferometry Kinetic Analysis of a Commercial Biotin-Labeled ADAM10 Antibody A commercial ELISA kit to detect ADAM10 (Biomatik) includes a biotinylated antibody that binds ADAM10. This enabled a comparable kinetic analysis by BLI of a commercial antibody with the same experimental conditions as used with the scFvs above (FIG. 11). Similar kinetic values were observed between the commercial antibody and the scFv antibody fragments (Table 6 and 7). A major difference however, was a significantly lower binding signal (greater than three-fold) was seen for the commercial antibody. This caused binding curves with significantly poorer fit due to lower signal-to-noise, and suggests that the scFvs disclosed herein may be more sensitive in detecting ADAM10 in BLI technology.

Epitope Mapping of the ADAM10 Surfaces Bound by the scFv Antibody Fragments

Figure 12:
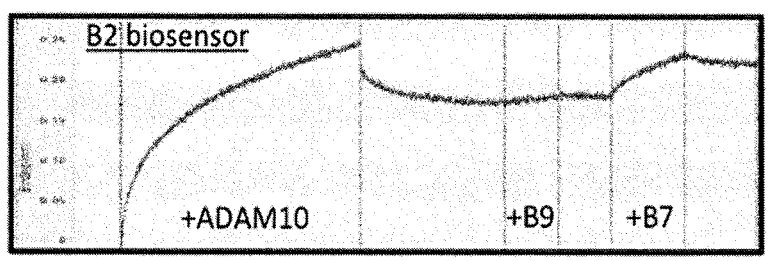
FIG. 12 shows epitope mapping of ADAM10 binding surfaces. BLI sensorgrams show the binding signal (nm) versus time (sec) for sequential interactions between ADAM10 and scFv antibody fragments. Streptavidin biosensors were derivatized with biotin-scFv-B2 (A), biotin-scFv-B7 (B), or biotin-scFv-B9 (C) and subsequently loaded with ADAM10 as indicated. Each of these sensors was then sequentially tested for binding to the other scFvs (i.e. +B2, +B7, +B9). A binding signal after the ADAM10 loading phase suggests recognition of an alternative epitope.
Figure 12:
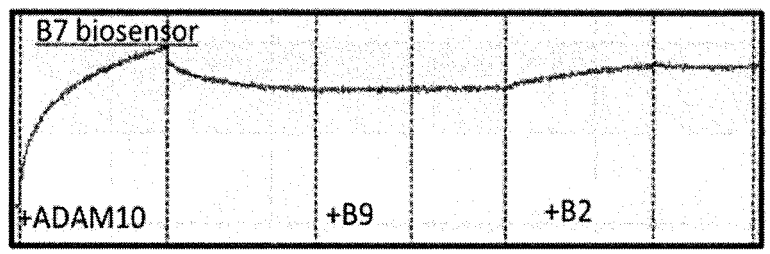
Figure 12:
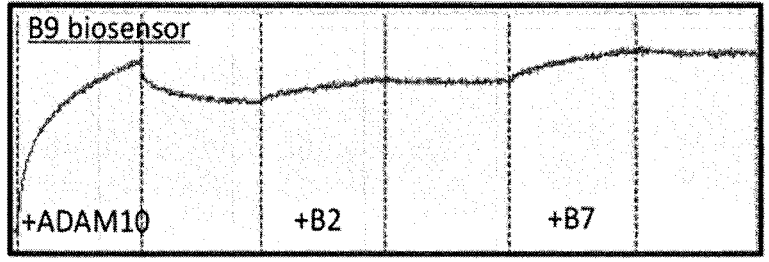

In order to develop a sandwich ELISA (or sandwich BLI) it was sought to determine if more than one ADAM10 epitope is recognized by the scFvs. To test this with BLI, streptavidin biosensors were loaded with one of the biotin-labeled scFv fragments and a secondary loading step was performed with ADAM10. These sensors were then sequentially dipped into the other two scFvs to determine if ADAM10 binding was still possible. FIG. 12 shows that scFv-B2 and scFv-B7 mapped to different surfaces, as they were able to bind ADAM10 simultaneously (FIGS. 12A and 12B). ScFv-B9 was able to bind ADAM10 along with either scFv-B2 or scFv-B7, but only provided it was loaded to the streptavidin biosensor and not the other orientation (FIG. 12A-C).

Materials and Methods:
ScFv Library Construction

An M13 phagemid vector was used as the destination for an scFv clone containing a $(G3S)_4$ polylinker that connects the heavy and light human $IgG_1$ sequences of the IgHV3-30 and IgKV1-16 germline genes, respectively. This scFv vector was then used as the single-stranded DNA template to perform oligonucleotide-mediated Kunkel mutagenesis to generate a synthetic scFv library of over $10^{10}$ unique members with randomized L3 and H3 CDRs. The remaining CDRs were designed with canonical consensus sequences that were determined through alignments of existing CDR loop structures in nature.

Phage-Display Selections

M13 filamentous phage display of the scFv fragment library was performed using an M13K07 helper phage system and conventional f1 bacteriophage handling and techniques. Phage display selections were performed with standard solid-phase immobilized target protocols. Briefly, 5 ug/ml of recombinant human ADAM10 (Biomatik, #RPU140010) was coated onto NUNC MaxiSorp Immunoplates and unbound surfaces were blocked with BSA. A 400-fold oversampling of the phage library ($400 \times 10^{12}$ total phage) was incubated with the target for two hours, at which time unbound phage was washed away and the target-bound phage was eluted and infected into *E. coli* for titers and overnight propagation. The second and third rounds of selection were performed similarly, except using propagated phage from the previous round of selection instead of the library. Random scFv phage clones from round 3 were selected for phage-based ELISA screening against ADAM10 (see below), and clones with appreciable signal over background were identified by DNA sequencing.

Phage-Based ELISA

Similar to the phage display screening methodology, ADAM10 was adsorbed to NUNC MaxiSorp Immunoplates and subsequently incubated with ~$10^{12}$ purified phage displaying an scFv clone. An anti-phage-horseradish peroxidase secondary antibody was then used to generate binding signals for each clone in duplicate, which was measured by colour development at an optical density of 450 nm (O.D. 450 nm) using a tetramethylbenzidine substrate (Thermo-Scientific, #34028).

Expression and Purification

ScFv antibody fragments identified in the selections were PCR amplified and sub-cloned with a homemade Gibson Assembly reaction mix into a protein expression vector. Antibody fragment protein was expressed in BL-21 E. coli using Overnight Express Instant TB media (Novagen, #71491-5), followed by protein L affinity chromatography. Each scFv fragment was covalently labeled with biotin using an N-hydroxysuccinamide amine-coupling reagent and manufacturer's instructions (EZ-link NHS biotin, Thermo-Scientific #20217).

Biolayer Interferometry

Biolayer interferometry was performed with an Octet RED384 instrument (ForteBio). The initial kinetics with unlabeled scFv was performed through coupling to AR2G biosensors per manufacturer instructions (ForteBio). These biosensors were then dipped into ADAM10 (500 nM and 166 nM) to generate the association curves, after which the sensors were moved into buffer alone to generate the corresponding dissociation curves. ForteBio Data Analysis 7.0 software was used for global curve fitting to generate the kinetic data. The kinetic analysis for biotin-conjugated scFvs was performed similarly, except that streptavidin biosensors (ForteBio) were used for immobilization, along with three ADAM10 concentrations (1000 nM, 500 nM, 166 nM). An equal loading (i.e. optical thickness) of the biosensors was performed in both kinetic experiments.

Epitope Mapping by Biolayer Interferometry

To determine if more than one ADAM10 epitope is recognized by the scFvs, streptavidin biosensors were loaded with one of the biotin-labeled scFvs to an optical thickness of ~1.0 nm and then with 500 nM ADAM10. These sensors were then sequentially dipped into the other unlabeled scFvs at 500 nM to test for a second ADAM10 binding curve, which indicates a separately recognized epitope.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Description of participants' head injuries

| #ID | Method of Injury | Initial Signs & Symptoms | | | Symptom Scale (#symptoms/total score) | Time from Injury to Collection |
|---|---|---|---|---|---|---|
| | | LOC | Balance | Cognitive | | |
| HMF27 | Helmet to helmet contact | No | Yes | Yes | 21/81 | 1 day |
| HMF28 | Unknown | No | No | No | 16/46 | 5 days |
| HFB15 | Elbow to head | No | No | Yes | 14/39 | 6 days |
| HFH13 | Collision with player head on but no head contact, whiplash | No | Yes | No | 6/13 | 2 days |

LOC = Loss of Consciousness

TABLE 2

CDR sequences of scFv clones binding ADAM10

| scFv | CDR L1 | CDR L2 | CDR L3 | CDR H1 | CDR H2 | CDR H3 |
|---|---|---|---|---|---|---|
| B2 | RASQGISNYLA (SEQ ID NO: 1) | YASSLQS (SEQ ID NO: 2) | QQSYYLPLT (SEQ ID NO: 3) | AASGFTFSSYGMH (SEQ ID NO: 6) | VISYDGSNKY (SEQ ID NO: 7) | ARWPAHFSHSHSSYYYYGFDV (SEQ ID NO: 8) |
| B7 | RASQGISNYLA (SEQ ID NO: 1) | YASSLQS (SEQ ID NO: 2) | QQVSSWPLT (SEQ ID NO: 4) | AASGFTFSSYGMH (SEQ ID NO: 6) | VISYDGSNKY (SEQ ID NO: 7) | ARYPPHGFDY (SEQ ID NO: 9) |
| B9 | RASQGISNYLA (SEQ ID NO: 1) | YASSLQS (SEQ ID NO: 2) | QQLYHPPLT (SEQ ID NO: 5) | AASGFTFSSYGMH (SEQ ID NO: 6) | VISYDGSNKY (SEQ ID NO: 7) | ARYSPYHYSHSVSYYYYGFDV (SEQ ID NO: 10) |

TABLE 3

ELISA binding signals (Absorbance at O.D. 450 nm) in duplicate for scFv clones and ADAM10

| scFv | BSA | ADAM10 | Average fold signal over background |
|---|---|---|---|
| B2 | 0.096, 0.079 | 4.000*, 4.000* | 45.7* |
| B7 | 0.084, 0.086 | 3.157, 3.137 | 37.0 |
| B9 | 0.075, 0.082 | 3.162, 3.444 | 42.1 |

*OD values were above the detectable limit and are therefore an underrepresentation of true values.

TABLE 4

Yield of purified scFv antibody fragments

| scFv | Concentration (mg/ml) | Yield (mg) per liter of culture |
|---|---|---|
| B2 | 0.452 | 6.6 |
| B7 | 0.682 | 10.0 |
| B9 | 0.695 | 10.2 |

TABLE 5

Kinetic parameters of the binding between scFv antibody fragments and ADAM10

| scFv | $K_D$ (M) | $K_D$ Error | $k_{on}$ (1/Ms) | $k_{on}$ Error | $k_{dis}$ (1/s) | $k_{dis}$ Error | $R^2$ |
|---|---|---|---|---|---|---|---|
| B2 | $1.46 \times 10^{-08}$ | $2.67 \times 10^{-10}$ | $1.28 \times 10^4$ | $1.23 \times 10^2$ | $1.87 \times 10^{-4}$ | $2.92 \times 10^{-6}$ | 0.985 |
| B7 | $7.52 \times 10^{-09}$ | $1.63 \times 10^{-10}$ | $1.24 \times 10^4$ | $7.93 \times 10^1$ | $9.30 \times 10^{-5}$ | $1.92 \times 10^{-6}$ | 0.995 |
| B9 | $9.32 \times 10^{-09}$ | $1.70 \times 10^{-10}$ | $1.24 \times 10^4$ | $8.16 \times 10^1$ | $1.15 \times 10^{-4}$ | $1.96 \times 10^{-6}$ | 0.993 |

TABLE 6

Kinetic parameters of the binding between biotin-labeled scFv antibody fragments and ADAM10

| scFv | $K_D$ (M) | $K_D$ Error | $k_{on}$ (1/Ms) | $k_{on}$ Error | $k_{dis}$ (1/s) | $k_{dis}$ Error | $R^2$ |
|---|---|---|---|---|---|---|---|
| B2 | $2.20 \times 10^{-08}$ | $4.20 \times 10^{-10}$ | $4.68 \times 10^4$ | $4.29 \times 10^2$ | $1.03 \times 10^{-3}$ | $1.72 \times 10^{-5}$ | 0.997 |
| B7 | $2.10 \times 10^{-08}$ | $4.07 \times 10^{-10}$ | $5.19 \times 10^4$ | $5.16 \times 10^2$ | $1.09 \times 10^{-3}$ | $1.81 \times 10^{-5}$ | 0.997 |
| B9 | $2.31 \times 10^{-08}$ | $3.81 \times 10^{-10}$ | $5.08 \times 10^4$ | $4.33 \times 10^2$ | $1.17 \times 10^{-3}$ | $1.66 \times 10^{-5}$ | 0.998 |

TABLE 7

Kinetic parameters of the binding between a commercial biotin-labeled antibody and ADAM10

| Antibody | $K_D$ (M) | $K_D$ Error | $k_{on}$ (1/Ms) | $k_{on}$ Error | $k_{dis}$ (1/s) | $k_{dis}$ Error | $R^2$ |
|---|---|---|---|---|---|---|---|
| Biomatik | $3.73 \times 10^{-08}$ | $1.22 \times 10^{-9}$ | $6.65 \times 10^4$ | $1.71 \times 10^3$ | $2.48 \times 10^{-3}$ | $4.99 \times 10^{-5}$ | 0.957 |

---

Table of Full Sequences

```
Coding sequence of scFv-B2:
TCCGATATCCAGATGACCCAGTCCCCGAGCTCCCTGTCCGCCTCTGTGGGCGATAGGGTCACCATCACCTGCCGTGCCAGTCAGGGC
ATCAGCAACTACCTGGCCTGGTATCAACAGAAACCAGGAAAAGCTCCGAAGCTTCTGATTTACGCCGCCAGCAGCCTGCAGTCTGGA
GTCCCTTCTCGCTTCTCTGGTAGCCGTTCCGGGACGGATTTCACTCTGACCATCAGCAGTCTGCAGCCGGAAGACTTCGCAACTTAT
TACTGTCAGCAATCTTACTACCTGCCTCTGACGTTCGGACAGGGTACCAAGGTGGAGATCAAAGGTGGTGGTTCTGGTGGTGGTTCT
GGTGGTGGTTCTGGTGGTGGTTCTGAGGTTCAGCTGGTGGAGTCTGGCGGTGGCCTGGTGCAGCCAGGGGGCTCACTCCGTTTGTCC
TGTGCAGCTTCTGGCTTCACCTTCAGCAGCTACGGCATGCACTGGGTGCGTCAGGCCCCGGGTAAGGGCCTGGAATGGGTTGCAGTG
ATCAGCTACGACGGCAGCAACAAGTATTATGCCGATAGCGTCAAGGGCCGTTTCACTATAAGCCGTGACAATTCCAAAAACACACTG
TACCTACAAATGAACAGCTTAAGAGCTGAGGACACTGCCGTCTATTATTGTGCTCGCTGGCCGGCTCATTTCTCTCATTCTCATTCT
AGTTACTACTACTACGGTTTCGACGTTTGGGGTCAAGGAACCCTGGTCACCGTCTCCTCG
(SEQ ID NO: 11)

Amino acid sequence of scFv-B2:
SDIQMTQSPSSLSASVGDRVTITCRASQGISNYLAWYQQKPGKAPKLLIYAASSLQSGVPSRFSGSRSGTDFTLTISSLQPEDFATY
YCQQSYYLPLTFGQGTKVEIKGGGSGGGSGGGSGGGSEVQLVESGGGLVQPGGSLRLSCAASGFTFSSYGMHWVRQAPGKGLEWVAV
ISYDGSNKYYADSVKGRFTISRDNSKNTLYLQMNSLRAEDTAVYYCARWPAHFSHSSYYYYGFDVWGQGTLVTVSS
(SEQ ID NO: 12)

Coding sequence of scFv-B7:
TCCGATATCCAGATGACCCAGTCCCCGAGCTCCCTGTCCGCCTCTGTGGGCGATAGGGTCACCATCACCTGCCGTGCCAGTCAGGGC
ATCAGCAACTACCTGGCCTGGTATCAACAGAAACCAGGAAAAGCTCCGAAGCTTCTGATTTACGCCGCCAGCAGCCTGCAGTCTGGA
```

-continued

Table of Full Sequences

```
GTCCCTTCTCGCTTCTCTGGTAGCCGTTCCGGGACGGATTTCACTCTGACCATCAGCAGTCTGCAGCCGGAAGACTTCGCAACTTAT
TACTGTCAGCAAGTTTCTTCTTGGCCTCTGACGTTCGGACAGGGTACCAAGGTGGAGATCAAAGGTGGTGGTTCTGGTGGTGGTTCT
GGTGGTGGTTCTGGTGGTGGTTCTGAGGTTCAGCTGGTGGAGTCTGGCGGTGGCCTGGTGCAGCCAGGGGGCTCACTCCGTTTGTCC
TGTGCAGCTTCTGGCTTCACCTTCAGCAGCTACGGCATGCACTGGGTGCGTCAGGCCCCGGGTAAGGGCCTGGAATGGGTTGCAGTG
ATCAGCTACGACGGCAGCAACAAGTATTATGCCGATAGCGTCAAGGGCCGTTTCACTATAAGCCGTGACAATTCCAAAAACACACTG
TACCTACAAATGAACAGCTTAAGAGCTGAGGACACTGCCGTCTATTATTGTGCTCGCTACCCGCCGCATGGTTTCGACTACTGGGGT
CAAGGAACCCTGGTCACCGTCTCCTCG
(SEQ ID NO: 13)

Amino acid sequence of scFv-B7:
SDIQMTQSPSSLSASVGDRVTITCRASQGISNYLAWYQQKPGKAPKLLIYAASSLQSGVPSRFSGSRSGTDFTLTISSLQPEDFATY
YCQQVSSWPLTFGQGTKVEIKGGGSGGGSGGGSGGGSEVQLVESGGGLVQPGGSLRLSCAASGFTFSSYGMHWVRQAPGKGLEWVAV
ISYDGSNKYYADSVKGRFTISRDNSKNTLYLQMNSLRAEDTAVYYCARYPPHGFDYWGQGTLVTVSS
(SEQ ID NO: 14)

Coding sequence of scFv-B9:
TCCGATATCCAGATGACCCAGTCCCCGAGCTCCCTGTCCGCCTCTGTGGGCGATAGGGTCACCATCACCTGCCGTGCCAGTCAGGGC
ATCAGCAACTACCTGGCCTGGTATCAACAGAAACCAGGAAAAGCTCCGAAGCTTCTGATTTACGCCGCCAGCAGCCTGCAGTCTGGA
GTCCCTTCTCGCTTCTCTGGTAGCCGTTCCGGGACGGATTTCACTCTGACCATCAGCAGTCTGCAGCCGGAAGACTTCGCAACTTAT
TACTGTCAGCAACTGTACCATCCGCCTCTGACGTTCGGACAGGGTACCAAGGTGGAGATCAAAGGTGGTGGTTCTGGTGGTGGTTCT
GGTGGTGGTTCTGGTGGTGGTTCTGAGGTTCAGCTGGTGGAGTCTGGCGGTGGCCTGGTGCAGCCAGGGGGCTCACTCCGTTTGTCC
TGTGCAGCTTCTGGCTTCACCTTCAGCAGCTACGGCATGCACTGGGTGCGTCAGGCCCCGGGTAAGGGCCTGGAATGGGTTGCAGTG
ATCAGCTACGACGGCAGCAACAAGTATTATGCCGATAGCGTCAAGGGCCGTTTCACTATAAGCCGTGACAATTCCAAAAACACACTG
TACCTACAAATGAACAGCTTAAGAGCTGAGGACACTGCCGTCTATTATTGTGCTCGCTACTCTCCGTACCATTACTCTCATTCTGTT
TCTTACTACTACTACGGTTTCGACGTTTGGGGTCAAGGAACCCTGGTCACCGTCTCCTCG
(SEQ ID NO: 15)

Amino acid sequence of scFv-B9:
SDIQMTQSPSSLSASVGDRVTITCRASQGISNYLAWYQQKPGKAPKLLIYAASSLQSGVPSRFSGSRSGTDFTLTISSLQPEDFATY
YCQQLYHPPLTFGQGTKVEIKGGGSGGGSGGGSGGGSEVQLVESGGGLVQPGGSLRLSCAASGFTFSSYGMHWVRQAPGKGLEWVAV
ISYDGSNKYYADSVKGRFTISRDNSKNTLYLQMNSLRAEDTAVYYCARYSPYHYSHSVSYYYYGFDVWGQGTLVTVSS
(SEQ ID NO: 16)
```

REFERENCES

Alvarez L. War veterans' concussions are often overlooked. New York Times. Aug. 25, 2008: A1

Altmeppen H C, Prox J, Puig B, Kluth M A, Bemreuther C, Thurm D, Jorissen E, Petrowitz B, Bartsch U, De Strooper B, Saftig P and Glatzel M. Lack of a-disintegrin-and-metalloproteinase ADAM10 leads to intracellular accumulation and loss of shedding of the cellular prion protein in vivo. Molecular Neurodegeneration 2011; 6:36.

Bauman R A, Ling G, Tong L, et al. An introductory characterization of a combat-casualty-care relevant swine model of closed head injury resulting from exposure to explosive blast. J Neurotrauma 2009; 26: 841-60

Belanger H G, Vanderploeg R D, Curtiss G, Warden D L (2007) Recent neuroimaging techniques in mild traumatic brain injury. J Neuropsychiatry Clin Neurosci 19: 5-20.

Boden B P, Tacchetti R L, Cantu R C, Knowles S B, Mueller F O (2007) Catastrophic head injuries in high school and college football players. Am J Sports Med 35: 1075-1081.

Brookings Institution, Saban Center for Middle East Policy. Iraq index: tracking variables of reconstruction and security in post-Saddam Iraq. Apr. 27, 2010

Burtis C A et al. Tietz Textbook of Clinical Chemistry and Molecular Diagnostics, 5th Edition 2012, page 106, Elsevier publication.

Caffey J. On the theory and practice of shaking infants: Its potential residual effects of permanent brain damage and mental retardation. American Journal of Diseases of Children 1972; 124(2): 161-9

Center for Disease Control and Prevention. 2012. Injury Prevention & Control: Traumatic Brain Injury, retrieved Apr. 16, 2013 from, http://www.cdc.gov/traumaticbraininjury/

Chavko M, Koller W A, Prusaczyk W K, et al. Measurement of blast wave by a miniature fiber optic pressure transducer in the rat brain. J Neurosci Methods 2007; 159: 277-81

Cole et al. "The EBV-Hybridoma Technique and its Application to Human Lung Cancer" in "Monoclonal Antibodies in Cancer Therapy", Allen R. Bliss, Inc. (1985), pages 77-96.

Daneshvar D H, Nowinski C J, McKee A C, Cantu R C (2011) The epidemiology of sport-related concussion. Clin Sports Med 30: 1-17, vii.

Elder G A, Mitsis E M, Ahlers S T, Cristian A. Blast-induced mild traumatic brain injury. Psychiatr Clin N Am 2010; 33: 757-81

Endres K and Fahrenholz F. Regulation of alpha-secretase ADAM10 expression and activity. Exp Brain Res 2012; 217: 343-352.

Forde C T, Karri S K, Young A M, Ogilvy C S (2014) Predictive markers in traumatic brain injury: opportunities for a serum biosignature. Br J Neurosurg 28: 8-15.

Gavett B E, Stem R A, McKee A C (2011) Chronic traumatic encephalopathy: a potential late effect of sport-related concussive and subconcussive head trauma. Clin Sports Med 30: 179-188, xi.

Guingab-Cagmat J D, Cagmat E B, Hayes R L, Anagli J (2013) Integration of proteomics, bioinformatics, and systems biology in traumatic brain injury biomarker discovery. Front Neurol 4: 61.

Guskiewicz K M, Register-Mihalik J, McCrory P, McCrea M, Johnston K, et al. (2013) Evidence-based approach to revising the SCAT2: introducing the SCAT3. Br J Sports Med 47: 289-293.

Halstead M E, Walter K D (2010) American Academy of Pediatrics. Clinical report-sport-related concussion in children and adolescents. Pediatrics 126: 597-615.

Harmon K G, Drezner J, Gammons M, Guskiewicz K, Halstead M, et al. (2013) American Medical Society for Sports Medicine position statement: concussion in sport. Clin J Sport Med 23: 1-18.

Hoge C W, McGurk D, Thomas J L, et al. Mild traumatic brain injury in U.S. soldiers returning from Iraq. N Engl J Med 2008; 358:453-6

Huse W D, Sastry L, Iverson S A, et al. Generation of a large combinatorial library of the immunoglobulin repertoire in phage lambda. Science. 1989; 246: 1275-81.

Jeter C B, Hergenroeder G W, Hylin M J, Redell J B, Moore A N, et al. (2013) Biomarkers for the diagnosis and prognosis of mild traumatic brain injury/concussion. J Neurotrauma 30: 657-670.

Köhler G, Milstein C. Continuous cultures of fused cells secreting antibody of predefined specificity. Nature 256, 495-497 (7 Aug. 1975).

Kozbor D, Roder J C. The production of monoclonal antibodies from human lymphocytes. Immunology Today [1983, 4(3):72-79].

Langlois J A, Rutland-Brown W, Wald M M (2006) The epidemiology and impact of traumatic brain injury: a brief overview. J Head Trauma Rehabil 21: 375-378.

Leibovici D, Gofrit O N, Stein M, et al. Blast injuries: bus versus open-air bombings—a comparative study of injuries in survivors of open-air versus confined-space explosions. J Trauma 1996; 41:1030-35

Mathivanan S, Hong J, and Simpson R J. Exosomes: Extracellular organelles important in intercellular communication. Journal of Proteomics. 2010; 73(10): 1907-1920.

McCafferty J, Jackson R H, Chiswell D J. Phage-enzymes: expression and affinity chromatography of functional alkaline phosphatase on the surface of bacteriophage. Protein Eng. 1991; 8: 955-61

McKee A C, Daneshvar D H, Alvarez V E, Stein T D. The neuropathology of sport. Acta Neuropathol. 2014; 127: 29-51.

Meehan W P, 3rd, Micheli L J (2011) Concussion results in deficits in neurocognitive functioning. Preface. Clin Sports Med 30: xvii-iii.

Meehan W P, 3rd, Mannix R C, O'Brien M J, Collins M W (2013) The prevalence of undiagnosed concussions in athletes. Clin J Sport Med 23: 339-342.

Okie, S. (2005) Traumatic brain injury in the war zone. N. Engl. J. Med. 352, 2043-2047.

Pham N, Sawyer T W, Wang Y, Jazii F R, Vair C, Taghibiglou C (2015 a) Primary blast-induced traumatic brain injury in rats leads to increased prion protein in plasma: a potential biomarker for blast-induced traumatic brain injury. J Neurotrauma. 32:58-65.

Pham N, Akonasu H, Shishkin R, Taghibiglou C (2015 b) Plasma soluble prion protein, a potential biomarker for sport-related concussions: a pilot study. PLoS One. 2015, 10:e0117286

Regan T. Report: High survival rate for US troops wounded in Iraq. Christian Science Monitor Nov. 29, 2004.

Schardin H. The physical principles of the effects of a detonation. German aviation medicine, World War II. Washington D.C.: Department of the US Air Force. Office of the Surgeon General; 1950: 1207-24.

Sharples R A, Vella L J, Nisbet R M, Naylor R, Perez K, Barnham K J, Masters C L, and Hill A F. Inhibition of γ-secretase causes increased secretion of amyloid precursor protein C-terminal fragments in association with exosomes. FASEB Journal. 2008; 22(5): 1469-1478.

Strathmann F G, Schulte S, Goerl K, Petron D J Blood-based biomarkers for traumatic brain injury: Evaluation of research approaches, available methods and potential utility from the clinician and clinical laboratory perspectives. Clin Biochem. 2014; 47(10-11):876-88.

Tanielian T, Jaycox L H. Invisible wonds of war: Psychological and cognitive injuries, their consequences and services to assist recovery. Rand Corp, MG 720-CCF, Santa Monica, Calif.

van der Pol E, Böing A N, Harrison P, Sturk A, and Nieuwland R. Classification, Functions, and Clinical Relevance of Extracellular Vesicles. Pharmacol Rev. 2012; 64:676-705.

Vingtdeux V and Marambaud P. Identification and biology of α-secretase. Journal of Neurochemistry. 2012; 120 (Suppl. 1): 34-45.

Ward R L, Clark M A, Lees J, Hawkins N J. Retrieval of human antibodies from phage-display libraries using enzymatic cleavage. J Immunol Methods. 1996; 189: 73-82.

Warden D. (2006) Military TBI during the Iraq and Afghanistan wars. J Head Trauma Rehabil 2006; 21: 398-402

Warren K M, Reeves T M, and Phillips L L. MT5-MMP, ADAM-10, and N-Cadherin Act in Concert To Facilitate Synapse Reorganization after Traumatic Brain Injury. Journal of Neurotrauma 29(10); 1922-1940.

Wolf S J, Bebarta V S, Bonnett C J, Pons P T, Cantrill S V. Blast injuries. The Lancet 2009: 374; 405-15

Wolf H, Frantal S, Pajenda G S, Salameh O, Widhalm H, et al. (2013) Predictive value of neuromarkers supported by a set of clinical criteria in patients with mild traumatic brain injury: S100B protein and neuron-specific enolase on trial: clinical article. J Neurosurg 118: 1298-1303.

Yarnell A M, Shaughness M C, Barry E S, et al. Blast traumatic brain injury in the rat using a blast overpressure model. Current Protocols in Neurosci 2013; 9.41: Supplement 62

Yokobori S, Hosein K, Burks S, Sharma I, Gajavelli S, et al. (2013) Biomarkers for the clinical differential diagnosis in traumatic brain injury—a systematic review. CNS Neurosci Ther 19: 556-565.

Zetterberg H, Smith D H, Blennow K (2013) Biomarkers of mild traumatic brain injury in cerebrospinal fluid and blood. Nat Rev Neurol 9: 201-210.

Zohar O, Lavy R, Zi X, Nelson T J, Hongpaisan J, Pick C G, Alkon D L. PKC activator therapeutic for mild traumatic brain injury in mice. Neurobiology of Disease 41(2); 329-337.

What is claimed is:

1. A method of detecting brain injury in a test subject comprising:
    (a) obtaining a blood sample from the test subject;
    (b) quantifying the amount of Disintegrin and metalloproteinase domain-containing protein 10 (ADAM10) indirectly or directly by fluorescence, radioactivity or absorbance; and
    (c) imaging the brain of the subject by CT scan, treating the subject by surgery, treating the subject with anti-epileptic drugs and/or treating the subject with a post-concussion protocol, wherein the subject follows the post-concussion protocol including rest, when there is an increase in the amount of ADAM10 compared to a control and wherein the control is a reference baseline level of ADAM10.

2. The method of claim 1 wherein the control is a reference baseline level of ADAM10 of the same test subject.

3. The method of claim 2, wherein the test subject is an athlete and the reference baseline level of ADAM10 of the subject is from the off-season.

4. The method of claim 1, wherein the control is a reference baseline level of ADAM10 of the general population or a reference baseline level of a population of similar age and/or of the same sex as the test subject.

5. The method of claim 1, wherein the blood sample from the test subject is obtained within and up to six days after occurrence of the brain injury event.

6. The method of claim 1, wherein the brain injury is a traumatic brain injury resulting from an explosion, fall, transportation accident, or sports-related concussion.

7. A method of monitoring a subject with a brain injury comprising:
    (i) (a) obtaining a blood sample from the subject at a first time point;
        (b) quantifying the amount of Disintegrin and metalloproteinase domain-containing protein 10 (ADAM10) at the first time point indirectly or directly by fluorescence, radioactivity or absorbance;
    (ii) (a) obtaining a blood sample from the subject at a second time point;
        (b) quantifying the amount of ADAM10 at the second time point indirectly or directly by fluorescence, radioactivity or absorbance; and
    (iii) imaging the brain of the subject by CT scan, treating the subject by surgery, treating the subject with anti-epileptic drugs and/or treating the subject with a post-concussion protocol, wherein the subject follows the post-concussion protocol including rest, when the amount of ADAM10 at the first time point is lower than the amount of ADAM10 at the second time point.

8. A method of determining whether a subject has suffered a brain injury due to an injury event comprising:
    (i) (a) obtaining a blood sample from the subject at a first time point prior to the injury event;
        (b) quantifying the amount of Disintegrin and metalloproteinase domain-containing protein 10 (ADAM 10) at the first time point indirectly or directly by fluorescence, radioactivity or absorbance;
    (iii) (a) obtaining a blood sample from the subject at a second time point after the injury event;
        (b) quantifying the amount of ADAM 10 at the second time point indirectly or directly by fluorescence, radioactivity or absorbance; and
    (iii) imaging the brain of the subject by CT scan, treating the subject by surgery, treating the subject with anti-epileptic drugs and/or treating the subject with a post-concussion protocol, wherein the subject follows the post-concussion protocol including rest, when the amount of ADAM10 at the first time point is lower than the amount of ADAM10 at the second time point.

9. The method of claim 8, wherein the second time point after the injury event is within and up to six days after the injury event.

10. A kit for analyzing a blood sample to detect brain injury, said kit comprising:
    (a) (i) an antibody or antibody fragment that detects an amount of ADAM10 in a blood sample; or
        (ii) an immobilized antibody or antibody fragment that binds to ADAM10 at a first position; and a detectable antibody or antibody fragment that binds to ADAM10 at a second position; and
    (b) instructions for use in analyzing the blood sample to detect brain injury,
    wherein the antibody or antibody fragment that detects an amount of ADAM10 in a blood sample, the antibody or antibody fragment that binds to ADAM10 at a first position, or the antibody or antibody fragment that binds to ADAM10 at a second position comprises:
    the heavy chain CDR sequences of SEQ ID NOs: 6, 7 and 8 and the light chain CDR sequences of SEQ ID NOs: 1, 2 and 3 thereof;
    the heavy chain CDR sequences of SEQ ID NOs: 6, 7 and 9 and the light chain CDR sequences of SEQ ID NOs: 1, 2 and 4;
    the heavy chain CDR sequences of SEQ ID NOs: 6, 7 and 10 and the light chain CDR sequences of SEQ ID NOs: 1, 2 and 5 thereof;
    the amino acid sequence as shown in SEQ ID NO:12 or is encoded by the nucleic acid sequence as shown in SEQ ID NO:11;
    the amino acid sequence as shown in SEQ ID NO:14 or is encoded by the nucleic acid sequence as shown in SEQ ID NO:13; or
    the amino acid sequence as shown in SEQ ID NO:16 or is encoded by the nucleic acid sequence as shown in SEQ ID NO:15.

11. The kit of claim 10, wherein
    a) the antibody or antibody fragment that binds to ADAM10 at the first position comprises the heavy chain CDR sequences of SEQ ID NOs: 6, 7 and 8 and the light chain CDR sequences of SEQ ID NOs: 1, 2 and 3 and the antibody or antibody fragment that binds to ADAM10 at the second position comprises the heavy chain CDR sequences of SEQ ID NOs: 6, 7 and 9 and the light chain CDR sequences of SEQ ID NOs: 1, 2 and 4; or the antibody or antibody fragment that binds to ADAM10 at a first position comprises the heavy chain CDR sequences of SEQ ID NOs: 6, 7 and 9 and the light chain CDR sequences of SEQ ID NOs: 1, 2 and 4 and the antibody or antibody fragment that binds to ADAM10 at the second position comprises the heavy chain CDR sequences of SEQ ID NOs: 6, 7 and 8 and the light chain CDR sequences of SEQ ID NOs: 1, 2 and 3;

b) the antibody or antibody fragment that binds to ADAM10 at the first position comprises the amino acid sequence as shown in SEQ ID NO:12 or is encoded by the nucleic acid sequence as shown in SEQ ID NO:11 and the antibody or antibody fragment that binds to ADAM10 at the second position comprises the amino acid sequence as shown in SEQ ID NO:14 or is encoded by the nucleic acid sequence as shown in SEQ ID NO:13, or the antibody or antibody fragment that binds to ADAM10 at the first position comprises the amino acid sequence as shown in SEQ ID NO:14 or is encoded by the nucleic acid sequence as shown in SEQ ID NO:13 and the antibody or antibody fragment that binds to ADAM10 at the second position comprises the amino acid sequence as shown in SEQ ID NO:12 or is encoded by the nucleic acid sequence as shown in SEQ ID NO:11;

c) the antibody or antibody fragment that binds to ADAM10 at the first comprises the heavy chain CDR sequences of SEQ ID NOs: 6, 7 and 8 and the light chain CDR sequences of SEQ ID NOs: 1, 2, and 3 and the antibody or antibody fragment that binds to ADAM10 at the second position comprises the heavy chain CDR sequences of SEQ ID NOs: 6, 7 and 10 and the light chain CDR sequences of SEQ ID NOs: 1, 2 and 5, or the antibody or antibody fragment that binds to ADAM10 at the first position comprises the heavy chain CDR sequences of SEQ ID NOs: 6, 7 and 10 and the light chain CDR sequences of SEQ ID NOs: 1, 2 and 5 and the antibody or antibody fragment that binds to ADAM10 at the second position comprises the heavy chain CDR sequences of SEQ ID NOs: 6, 7 and the light chain CDR sequences of SEQ ID NOs: 1, 2, and 3;

d) the antibody or antibody fragment that binds to ADAM10 at the first position comprises the amino acid sequence as shown in SEQ ID NO:12 or is encoded by the nucleic acid sequence as shown in SEQ ID NO:11 and the antibody or antibody fragment that binds to ADAM10 at the second position comprises the amino acid sequence as shown in SEQ ID NO:16 or is encoded by the nucleic acid sequence as shown in SEQ ID NO:15, or the antibody or antibody fragment that binds to ADAM10 at the first position comprises the amino acid sequence as shown in SEQ ID NO:16 or is encoded by the nucleic acid sequence as shown in SEQ ID NO:15 and the antibody or antibody fragment that binds to ADAM10 at the second position comprises the amino acid sequence as shown in SEQ ID NO:12 or is encoded by the nucleic acid sequence as shown in SEQ ID NO:11;

e) the antibody or antibody fragment that binds to ADAM10 at the first position comprises the heavy chain CDR sequences of SEQ ID NOs: 6, 7 and 9 and the light chain CDR sequences of SEQ ID NOs: 1, 2, and 4 and the antibody or antibody fragment that binds to ADAM10 at the second position comprises the heavy chain CDR sequences of SEQ ID NOs: 6, 7 and 10 and the light chain CDR sequences of SEQ ID NOs: 1, 2 and 5, or the antibody or antibody fragment that binds to ADAM10 at the first position comprises the heavy chain CDR sequences of SEQ ID NOs: 6, 7 and 10 and the light chain CDR sequences of SEQ ID NOs: 1, 2 and 5 and the antibody or antibody fragment that binds to ADAM10 at the second position comprises the heavy chain CDR sequences of SEQ ID NOs: 6, 7 and 9 and the light chain CDR sequences of SEQ ID NOs: 1, 2, and 4;

or f) the antibody or antibody fragment that binds to ADAM10 at the first position comprises the amino acid sequence as shown in SEQ ID NO:14 or is encoded by the nucleic acid sequence as shown in SEQ ID NO:13 and the antibody or antibody fragment that binds to ADAM10 at the second position comprises the amino acid sequence as shown in SEQ ID NO:16 or is encoded by the nucleic acid sequence as shown in SEQ ID NO:15, or the antibody or antibody fragment that binds to ADAM10 at the first position comprises the amino acid sequence as shown in SEQ ID NO:16 or is encoded by the nucleic acid sequence as shown in SEQ ID NO:15 thereof and the antibody or antibody fragment that binds to ADAM10 at the second position comprises the amino acid sequence as shown in SEQ ID NO:14 or is encoded by the nucleic acid sequence as shown in SEQ ID NO:13.

12. An isolated antibody or antibody fragment comprising
a) the heavy chain CDR sequences of SEQ ID NOs: 6, 7 and 8 and the light chain CDR sequences of SEQ ID NOs: 1, 2 and 3;
b) the heavy chain CDR sequences of SEQ ID NOs: 6, 7 and 9 and the light chain CDR sequences of SEQ ID NOs: 1, 2 and 4;
c) the heavy chain CDR sequences of SEQ ID NOs: 6, 7 and 10 and the light chain CDR sequences of SEQ ID NOs: 1, 2 and 5;
d) the amino acid sequence as shown in SEQ ID NO:12 or is encoded by the nucleic acid sequence as shown in SEQ ID NO:11;
e) the amino acid sequence as shown in SEQ ID NO:14 or is encoded by the nucleic acid sequence as shown in SEQ ID NO:13; or
f) the amino acid sequence as shown in SEQ ID NO:16 or is encoded by the nucleic acid sequence as shown in SEQ ID NO:15.

\* \* \* \* \*

SEQUENCE LISTING

<160> NUMBER OF SEQ ID NOS: 16

<210> SEQ ID NO 1
<211> LENGTH: 11
<212> TYPE: PRT
<213> ORGANISM: Homo sapiens

<400> SEQUENCE: 1

Arg Ala Ser Gln Gly Ile Ser Asn Tyr Leu Ala
1               5                   10

<210> SEQ ID NO 2
<211> LENGTH: 8
<212> TYPE: PRT
<213> ORGANISM: Homo sapiens

<400> SEQUENCE: 2

Tyr Ala Ala Ser Ser Leu Gln Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gln Gln Ser Tyr Tyr Leu Pro Leu Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Gln Gln Val Ser Ser Trp Pro Leu Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gln Gln Leu Tyr His Pro Pro Leu Thr
1               5

<210> SEQ ID NO 6
<211> LENGTH: 13
<212> TYPE: PRT
<213> ORGANISM: Homo sapiens

<400> SEQUENCE: 6

Ala Ala Ser Gly Phe Thr Phe Ser Ser Tyr Gly Met His
1               5                   10

<210> SEQ ID NO 7
<211> LENGTH: 10
<212> TYPE: PRT
<213> ORGANISM: Homo sapiens

<400> SEQUENCE: 7

Val Ile Ser Tyr Asp Gly Ser Asn Lys Tyr
1               5                   10

```
<210> SEQ ID NO 8
<211> LENGTH: 21
<212> TYPE: PRT
<213> ORGANISM: Artificial Sequence
<220> FEATURE:
<223> OTHER INFORMATION: Synthetic

<400> SEQUENCE: 8

Ala Arg Trp Pro Ala His Phe Ser His Ser His Ser Tyr Tyr Tyr
1               5                   10                  15

Tyr Gly Phe Asp Val
            20

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Ala Arg Tyr Pro Pro His Gly Phe Asp Tyr
1               5                   10

<210> SEQ ID NO 10
<211> LENGTH: 21
<212> TYPE: PRT
<213> ORGANISM: Artificial Sequence
<220> FEATURE:
<223> OTHER INFORMATION: Synthetic

<400> SEQUENCE: 10

Ala Arg Tyr Ser Pro Tyr His Tyr Ser His Ser Val Ser Tyr Tyr
1               5                   10                  15

Tyr Gly Phe Asp Val
            20

<210> SEQ ID NO 11
<211> LENGTH: 756
<212> TYPE: DNA
<213> ORGANISM: Artificial Sequence
<220> FEATURE:
<223> OTHER INFORMATION: Synthetic

<400> SEQUENCE: 11
tccgatatcc agatgaccca gtccccgagc tccctgtccg cctctgtggg cgatagggtc      60
accatcacct gccgtgccag tcagggcatc agcaactacc tggcctggta tcaacagaaa     120
ccaggaaaag ctccgaagct tctgatttac gccgccagca gcctgcagtc tggagtccct     180
tctcgcttct ctggtagccg ttccgggacg gatttcactc tgaccatcag cagtctgcag     240
ccggaagact tcgcaactta ttactgtcag caatcttact acctgcctct gacgttcgga     300
cagggtacca aggtggagat caaaggtggt ggttctggtg gtggttctgg tggtggttct     360
ggtggtggtt ctgaggttca gctggtggag tctgcggtg gcctggtgca gccagggggc      420
tcactccgtt tgtcctgtgc agcttctggc ttcaccttca gcagctacgg catgcactgg     480
gtgcgtcagg cccgggtaa gggcctggaa tgggttgcag tgatcagcta cgacggcagc     540
aacaagtatt atgccgatag cgtcaagggc cgtttcacta agcccgtga caattccaaa     600 aacacactgt acctacaaat gaacagctta agagctgagg acactgccgt ctattattgt     660
gctcgctggc cggctcattt ctctcattct cattctagtt actactacta cggtttcgac     720
gtttggggtc aaggaaccct ggtcaccgtc tcctcg                                756
```

<210> SEQ ID NO 12
<211> LENGTH: 252
<212> TYPE: PRT
<213> ORGANISM: Artificial Sequence
<220> FEATURE:
<223> OTHER INFORMATION: Synthetic

<400> SEQUENCE: 12

```
Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Tyr Tyr Leu Pro
                85                  90                  95

Leu Thr Phe Gly Gln Gly Thr Lys Val Glu Ile Lys Gly Gly Gly Ser
            100                 105                 110

Gly Gly Gly Ser Gly Gly Gly Ser Gly Gly Gly Ser Glu Val Gln Leu
        115                 120                 125

Val Glu Ser Gly Gly Gly Leu Val Gln Pro Gly Gly Ser Leu Arg Leu
130                 135                 140

Ser Cys Ala Ala Ser Gly Phe Thr Phe Ser Ser Tyr Gly Met His Trp
145                 150                 155                 160

Val Arg Gln Ala Pro Gly Lys Gly Leu Glu Trp Val Ala Val Ile Ser
                165                 170                 175

Tyr Asp Gly Ser Asn Lys Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Arg Trp Pro
    210                 215                 220

Ala His Phe Ser His Ser His Ser Ser Tyr Tyr Tyr Gly Phe Asp
225                 230                 235                 240

Val Trp Gly Gln Gly Thr Leu Val Thr Val Ser Ser
                245                 250
```

<210> SEQ ID NO 13
<211> LENGTH: 723
<212> TYPE: DNA
<213> ORGANISM: Artificial Sequence
<220> FEATURE:
<223> OTHER INFORMATION: Synthetic

<400> SEQUENCE: 13

```
tccgatatcc agatgaccca gtccccgagc tccctgtccg cctctgtggg cgatagggtc      60
accatcacct gccgtgccag tcagggcatc agcaactacc tggcctggta tcaacagaaa     120
ccaggaaaag ctccgaagct tctgatttac gccgccagca gcctgcagtc tggagtccct     180
tctcgcttct ctggtagccg ttccgggacg gatttcactc tgaccatcag cagtctgcag     240
ccggaagact tcgcaactta ttactgtcag caagtttctt cttggcctct gacgttcgga     300
```

```
cagggtacca aggtggagat caaaggtggt ggttctggtg gtggttctgg tggtggttct    360
ggtggtggtt ctgaggttca gctggtggag tctggcggtg gcctggtgca gccagggggc    420
tcactccgtt tgtcctgtgc agcttctggc ttcaccttca gcagctacgg catgcactgg    480
gtgcgtcagg ccccgggtaa gggcctggaa tgggttgcag tgatcagcta cgacggcagc    540
aacaagtatt atgccgatag cgtcaagggc cgtttcacta taagccgtga caattccaaa    600
aacacactgt acctacaaat gaacagctta gagctgagg acactgccgt ctattattgt     660
gctcgctacc cgccgcatgg tttcgactac tggggtcaag aaccctggt caccgtctcc     720 tcg                                                                    723
```

<210> SEQ ID NO 14
<211> LENGTH: 241
<212> TYPE: PRT
<213> ORGANISM: Artificial Sequence
<220> FEATURE:
<223> OTHER INFORMATION: Synthtetic

<400> SEQUENCE: 14

```
Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Val Ser Ser Trp Pro
                85                  90                  95

Leu Thr Phe Gly Gln Gly Thr Lys Val Glu Ile Lys Gly Gly Gly Ser
            100                 105                 110

Gly Gly Gly Ser Gly Gly Gly Ser Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Ser Ser Tyr Gly Met His Trp
145                 150                 155                 160

Val Arg Gln Ala Pro Gly Lys Gly Leu Glu Trp Val Ala Val Ile Ser
                165                 170                 175

Tyr Asp Gly Ser Asn Lys Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Arg Tyr Pro
    210                 215                 220

Pro His Gly Phe Asp Tyr Trp Gly Gln Gly Thr Leu Val Thr Val Ser
225                 230                 235                 240

Ser
```

<210> SEQ ID NO 15
<211> LENGTH: 756
<212> TYPE: DNA
<213> ORGANISM: Artificial Sequence
<220> FEATURE:

<223> OTHER INFORMATION: Synthetic

<400> SEQUENCE: 15

```
tccgatatcc agatgaccca gtccccgagc tccctgtccg cctctgtggg cgatagggtc    60
accatcacct gccgtgccag tcagggcatc agcaactacc tggcctggta tcaacagaaa   120
ccaggaaaag ctccgaagct tctgatttac gccgccagca gcctgcagtc tggagtccct   180
tctcgcttct ctggtagccg ttccgggacg gatttcactc tgaccatcag cagtctgcag   240
ccggaagact tcgcaactta ttactgtcag caactgtacc atccgcctct gacgttcgga   300
cagggtacca aggtggagat caaaggtggt ggttctggtg gtggttctgg tggtggttct   360
ggtggtggtt ctgaggttca gctggtggag tctggcggtg gcctggtgca gccagggggc   420
tcactccgtt tgtcctgtgc agcttctggc ttcaccttca gcagctacgg catgcactgg   480
gtgcgtcagg ccccgggtaa gggcctggaa tgggttgcag tgatcagcta cgacggcagc   540
aacaagtatt atgccgatag cgtcaagggc cgtttcacta taagccgtga caattccaaa   600
aacacactgt acctacaaat gaacagctta agagctgagg acactgccgt ctattattgt   660
gctcgctact ctccgtacca ttactctcat tctgtttctt actactacta cggtttcgac   720
gtttggggtc aaggaaccct ggtcaccgtc tcctcg                            756
```

<210> SEQ ID NO 16
<211> LENGTH: 252
<212> TYPE: PRT
<213> ORGANISM: Artificial Sequence
<220> FEATURE:
<223> OTHER INFORMATION: Synthetic

<400> SEQUENCE: 16

```
Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Ser Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln Leu Tyr His Pro Pro
                85                  90                  95

Leu Thr Phe Gly Gln Gly Thr Lys Val Glu Ile Lys Gly Gly Gly Ser
            100                 105                 110

Gly Gly Gly Ser Gly Gly Gly Ser Gly Gly Gly Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Thr Phe Ser Ser Tyr Gly Met His Trp
145                 150                 155                 160

Val Arg Gln Ala Pro Gly Lys Gly Leu Glu Trp Val Ala Val Ile Ser
                165                 170                 175

Tyr Asp Gly Ser Asn Lys Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205
```

```
Ser Leu Arg Ala Glu Asp Thr Ala Val Tyr Tyr Cys Ala Arg Tyr Ser
    210                 215                 220
Pro Tyr His Tyr Ser His Ser Val Ser Tyr Tyr Tyr Gly Phe Asp
225             230                 235                 240
Val Trp Gly Gln Gly Thr Leu Val Thr Val Ser Ser
                245                 250
```